United States Patent
Metz, Jr. et al.

(10) Patent No.: US 7,402,672 B2
(45) Date of Patent: Jul. 22, 2008

(54) SUBSTITUTED 1H-PYRROLO[3,2-B, 3,2-C, AND 2,3-C]PYRIDINE-2-CARBOXAMIDES AND RELATED ANALOGS AS INHIBITORS OF CASEIN KINASE I EPSILON

(75) Inventors: William A. Metz, Jr., Bridgewater, NJ (US); Frank Halley, Chaville (FR); Gilles Dutruc-Rosset, Paris (FR); Yong Mi Choi-Sledeski, Belle Mead, NJ (US); Gregory Bernard Poli, Bethlehem, PA (US); David Marc Fink, Lebanon, NJ (US); Gilles Doerflinger, Les Ulis (FR); Bao-Guo Huang, Bridgewater, NJ (US); Ann Marie Gelormini, Hillsborough, NJ (US); Juan Antonio Gamboa, New York, NY (US); Andrew Giovanni, Flemington, NJ (US); Joachim E. Roehr, Bernardsville, NJ (US); Joseph T. Tsay, Bridgewater, NJ (US); Fernando Camacho, Union, NJ (US); William Joseph Hurst, Oxford, NJ (US); Stephen Wayne Harnish, Wharton, NJ (US); Yulin Chiang, Convent Station, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 497 days.

(21) Appl. No.: 11/001,533

(22) Filed: Dec. 1, 2004

(65) Prior Publication Data
US 2005/0131012 A1 Jun. 16, 2005

Related U.S. Application Data

(60) Provisional application No. 60/528,764, filed on Dec. 11, 2003.

(51) Int. Cl.
*C07D 471/00* (2006.01)
(52) U.S. Cl. .................................................. 546/113
(58) Field of Classification Search ................ 546/113; 549/113
See application file for complete search history.

(56) References Cited

U.S. PATENT DOCUMENTS 5,527,819 A 6/1996 Williams et al.

FOREIGN PATENT DOCUMENTS

| EP | 0186367 | 7/1986 |
|---|---|---|
| WO | WO 94/19321 | 9/1994 |
| WO | WO 95/33748 | 12/1995 |
| WO | WO 99/28313 | 6/1999 |
| WO | WO 03/029252 A1 | 4/2003 |
| WO | WO 03/078435 | 9/2003 |
| WO | WO 03/080608 | 10/2003 |

OTHER PUBLICATIONS

Camacho F et al, Casein Kinase 1 and Circadian Rhythms: Effects of Manipulation of CKI Epsilon Activity on Period, Soc. for Neuroscience, Nov. 8-12, 2003, New Orleans, LA; Program No. 284.3. 2003 Abstract Viewer/Itinerary Planner. Washington, DC.

Harnish S et al, Molecular Circadian Rhythms in Rat-1 Fibroblasts II: Pharmacological Manipulation of Period and Phase. , Soc. for Neuroscience, Nov. 8-12, 2003, New Orleans, LA, Program No. 284.2. 2003 Abstract Viewer/Itinerary Planner. Washington, DC: Society for Neuroscience, 2003.

Hurst WJ et al, Molecular Circadian Rhythms in Rat-1 Fibroblasts I: Developing A High-Throughput Assay. Program No. 284.1. 2003 , Soc. For Neuroscience Meeting, Nov. 8-12, 2003, New Orleans, LA.

*Primary Examiner*—D. Margaret Seaman
*Assistant Examiner*—Nizal S. Chandrakumar
(74) *Attorney, Agent, or Firm*—Lawrence L. Martin; Craig M. Bell

(57) ABSTRACT

The present invention discloses and claims compounds of formula (I)

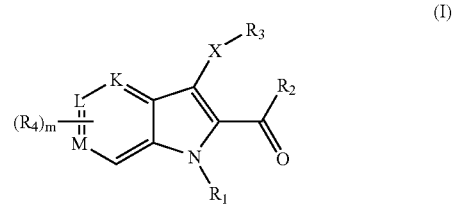

as inhibitors of human casein kinase IF, and methods of using said compounds of formula (I) for treating central nervous system diseases and disorders including mood disorders and sleep disorders. Pharmaceutical compositions comprising compounds of formula (I) and methods for the preparation of compounds of formula (I) are also disclosed and claimed.

11 Claims, No Drawings

SUBSTITUTED 1H-PYRROLO[3,2-B, 3,2-C, AND 2,3-C]PYRIDINE-2-CARBOXAMIDES AND RELATED ANALOGS AS INHIBITORS OF CASEIN KINASE I EPSILON

This application claims the benefit of U.S. Provisional Application No. 60/528,764, filed Dec. 11, 2003.

BACKGROUND OF THE INVENTION

1. Field of the Invention

This present invention relates to a series of substituted 1H-pyrrolo[3,2-b]pyridine-2-carboxamides, 1H-pyrrolo[3,2-c]pyridine-2-carboxamides and 1H-pyrrolo[2,3-c]pyridine-2-carboxamides. More specifically the invention relates to 3-arylthio-substituted and 3-heterocyclethio-substituted 1H-pyrrolo[3,2-b]pyridine-2-carboxamides, 1H-pyrrolo[3,2-c]pyridine-2-carboxamides and 1H-pyrrolo[2,3-c]pyridine-2-carboxamides, and related analogs. The invention also relates to methods of making these compounds. The compounds of the invention are inhibitors of human casein kinase IF phosphorylation activity and are therefore useful, as pharmaceutical agents, especially in the treatment and/or prevention of diseases and disorders associated with the central nervous system.

2. Description of the Art

Rhythmic variations in behavior are displayed by many organisms, ranging from single cells to man. When the rhythm persists under constant conditions, and has a period of about one day, depending little on temperature, the rhythm is called "circadian" (Konopka, R. J. and Benzer, S. (1971) Proc. Nat. Acad. Sci. USA 68, 2112-2116).

Circadian rhythms are generated by endogenous biological pacemakers (circadian clocks) and are present in most living organisms including humans, fungi, insects and bacteria (Dunlap, J. C. (1999) Cell 96, 271-290; Hastings, J. W. et al. Circadian Rhythms, The Physiology of Biological Timing. In: Prosser, C. L. ed. Neural and Integrative Animal Physiology, New York: Wiley-Liss (1991) 435-546; Allada, R. et al. (1998) Cell 93, 791-804; Kondo et al. (1994) Science 266, 1233-1236; Crosthwaite, S. K. et al. (1997) Science 276, 763-769; Shearman, L. P. et al. (1997) Neuron, 19, 1261-1269). Circadian rhythms are self-sustaining and constant even under conditions of total darkness, but can be synchronized (entrained) to a new day/night regime by environmental signals such as light and temperature cycles (Pittendrigh, C. S. (1993) Annu. Rev. Physiol., 55, 16-54; Takahashi, J. S. (1995) Annu. Rev. Neurosci. 18, 531-553; Albrecht, U. et al. (1997) Cell, 91, 1055-1064). Circadian clocks are essential for maintaining biological rhythms and regulate a variety of circadian behaviors such as daily fluctuations in behavior, food intake and the sleep/wake cycle, as well as physiological changes such as hormone secretion and fluctuations in body temperature (Hastings, M. (1997) Trends Neurosci. 20, 459-464; Reppert, S. M. and Weaver, D. R. (1997) Cell 89, 487-490).

Genetic and molecular studies in the fruit fly *Drosophila melanogaster* led to elucidation of some of the genes involved in circadian rhythmicity. These studies led to recognition of a pathway that is closely auto-regulated and comprised of a transcription/translation-based negative feed back loop (Dunlap, J. C. (1999) Cell, 96, 271-290; Dunlap, J. C. (1996) Annu. Rev. Genet 30, 579-601; Hall, J. C. (1996) Neuron, 17, 799-802). The core elements of the circadian oscillator in *Drosophila* consists of two stimulatory proteins dCLOCK/dBMAL (CYCLE) and two inhibitory proteins dPERIOD (dPER) and dTIMELESS (dTIM). dCLOCK and dBMAL heterodimerize forming the transcription factor dCLOCK/dBMAL that promotes expression of two genes termed *Drosophila* Period (dper) and *Drosophila* Timeless (dtim). Ultimately the mRNAs from these genes are transcribed to afford the proteins dPER and dTIM, respectively. For several hours the protein products dPER and dTIM are synthesized and phosphorylated in the cytoplasm, reach a critical level, and form heterodimers that are translocated into the nucleus. Once in the nucleus dPER and dTIM function as negative regulators of their own transcription, accumulation of dPER and dTIM declines, and activation of dper and dtim by dCLOCK/dBMAL starts again (Zylka, M. J. et al. (1998) Neuron 20, 1103-1110; Lowrey, P. L. et al. (2000)288, 483-491). The dper gene has been shown to be a necessary element in controlling circadian rhythms in adult eclosion (the emergence of the adult fly from the pupa) behavior and locomotor activity (Konopka, R. J., & Benzer, S. (1971) Proc. Natl. Acad. Sci. USA, 68, 2112-2116). Missense mutations of the per gene can either shorten (per$^S$) or lengthen (per$^L$) the period of circadian rhythms, while nonsense mutations (per$^O$) cause arrhythmicity in their behaviors (Hall, J. C. (1995) Trends Neurosci. 18, 230-240).

In mammals, the suprachiasmatic nuclei (SCN) of the anterior hypothalamus are the site of a master biological clock (for review see Panda et al, (2002) Nature 417, 329-335; Reppert, S. M. and Weaver, D. R. (1997) Cell, 89, 487-490). The SCN clock is entrained to the 24 hour day by the daily light-dark cycle, with light acting through both direct and indirect retina-to-SCN pathways (Klein, D. C. et al. (1991) Suprachiasmatic Nuclei: The Mind's Clock, Oxford Univeristy Press, New York). In the SCN of rodents, three Per genes have been identified and cloned, and are designated as mouse Per1 (mPer1), mPer2 and mPer3. The protein products of these mammalian genes (mPER1, mPER2, mPER3) share several regions of homology to each other, and each mammalian Per gene encodes a protein with a protein dimerization domain designated as PAS (PAS is an acronym for the first three proteins PER, ARNT and SIM found to share this functionally important dimerization domain) that is highly homologous to the PAS domain of insect PER. All Per messenger RNAs (mRNAs) and protein levels oscillate during the circadian day and are intimately involved in both positive and negative regulation of the biological clock, but only mPER1 and mPER2 oscillate in response to light (Zylka, M. J. et al. (1998) Neuron 20, 1103-1110.; Albrecht, U. et al., (1997) Cell 91, 1055-1064; Shearman, L. P. et al. (1997) Neuron 19, 1261-1269). The mammalian homolog of the *Drosophila* tim gene was cloned and designated as mTim. However, there was no evidence for mPER-mTIM interactions analogous to those observed in *Drosophila*, and it was suggested that PER-PER interactions may have replaced the function of PER-TIM dimers in the molecular workings of the mammalian circadian clock (Zylka, M. J. et al., (1998) Neuron 21, 1115-1122). Another possibility is that rhythms in PER1 and PER2 form negative feedback loops that regulate the transcriptional activity of the Clock protein (via their PAS domains), which, in turn, drives expression of either or both Per genes (Shearman, L. P. et al. (1997) Neuron 19, 1261-1269).

Understanding the roles of the three mPer genes in the mammalian clockwork has been the subject of much investigation. The structural homology of the mPER proteins to dPER led to the expectation that the mPER proteins would function as negative elements in the mammalian feedback loop. PER1 is believed to be involved in the negative regulation of its own transcription in the feedback loop, but recent evidence points to it being involved in the input pathway (Hastings, M. H. et al. (1999) Proc. Natl. Acad. Sci. USA 26, 15211-15216). PER2 is the most well characterized protein, and mPER2 mutant mice (mPer2$^{Brdm1}$), lacking 87 residues at the carboxyl portion of the PAS dimerization domain, have a shortened circadian cycle in normal light-dark settings, but show arrhythmicity in complete darkness. The mutation also diminishes the oscillating expression of both mPer1 and mPer2 in the SCN, indicating that mPer2 may regulate mPer1 in vivo (Zheng, B. et al. (1999) Nature 400, 169-173). PER2 has been shown to have a dual function in the regulation of the "gears" of the central clock (Shearman, L. P. et al. (2000) Science 288, 1013-1018). In that study, PER2 was shown to bind to cryptochrome (CRY) proteins and translocate to the nucleus where CRY negatively regulated transcription driven by the CLOCK and BMAL1 positive transcriptional complexes. Upon nuclear entry, PER2 initiated the positive arm of the clock by positively regulating BMAL1 transcription by a yet unidentified mechanism. The function of PER3 is poorly understood; however, in mPer3 knockout mice a subtle effect on circadian activity is observed, and therefore PER3 has been suggested to be involved in the circadian controlled output pathways (Shearman, L. P. et al. (2000) Mol. Cell. Biol. 17, 6269-6275). It has been reported that mPER proteins interact with each other and that mPER3 can serve as a carrier of mPER1 and mPER2 to bring them into the nucleus which is critical for the generation of circadian signals in the SCN (Kume, K. et al. (1999) Cell 98, 193-205; Takano, A. et al. (2000), FEBS Letters, 477, 106-112).

Phosphorylation of the components of the circadian clock has been postulated to regulate the duration of the cycle. The first genetic evidence that a specific protein kinase regulates the *Drosophila* circadian rhythm was the discovery of the novel gene doubletime (dbt), encoding a protein serine/threonine kinase (Price J. L. et al. (1998) Cell 94, 83-95; Kloss B. et al. (1998) Cell 94, 97-107). Missense mutations in the dbt result in an altered circadian rhythm. Null alleles of dbt result in hypophosphorylation of dPER and arrhythmia.

The mammalian kinases most closely related to DBT are casein kinase Iε (CKIε) and casein kinase Iδ (CKIδ). Both kinases have been shown to bind to mPER1, and several studies have shown that CKIε phosphorylates both mouse and human PER1 (Price J. L. et al. (1998) Cell 94, 83-95; Kloss B. et al. (1998) Cell 94, 97-107). In a study with human embryonic kidney 293T cells co-transfected with wild-type hCKIε, hPER1 showed a significant increase in phosphorylation (evidenced by a shift in molecular mass). In this study, the phosphorylated hPER1 had a half-life of approximately twelve hours whereas unphosphorylated hPER1 remained stable in the cell for more that 24 hours, suggesting phosphorylation of hPER1 leads to a decrease in protein stability (Kessler, G. A. et al. (2000) NeuroReport, 11, 951-955). Another study also showed the consequence of PER1 phosphorylation by hCKIε includes both cytoplasmic retention, nuclear translocation, and protein instability (Vielhaber, E. et al. (2000) Mol. Cell. Biol. 13, 4888-4899; Takano, A. et al. (2000) FEBS Letters 477, 106-112).

There has been no biochemical reason to choose between CKIε or CKIδ as a potential regulator in mammals until Lowery et al. [(2000) Science 288, 483-491] found that in the Syrian Golden hamster, semidominant mutations in CKIε (tau mutation, Ralph, M. R. and Menaker, M. (1988) Science 241, 1225-1227) caused a shortened circadian day in both heterozygous (22 h) and homozygous animals (20 h). In this instance, reduced levels of CKIε activity resulted in less PER phosphorylation with presumably higher levels of cytoplasmic PER protein leading to enhanced nuclear entry and altered circadian cycles. More recently, it has been suggested that CKIδ may also be involved in regulating circadian rhythmicity by post-translation modification of mammalian clock proteins hPER1 and hPER2 [Camacho, F. et al., (2001) FEBS Letters 489(2,3), 159-165]. Thus, small molecule inhibitors of CKIε and/or CKIδ provide a novel means to alter circadian rhythm. As discussed below, the alteration of circadian rhythm may find utility for the treatment of sleep or mood disorders.

U.S. Pat. No. 6,555,328 B1 discloses screening methods in cells to identify compounds that alter circadian rhythms based on a test compound altering the ability of human casein kinase 1ε and/or human casein kinase 1δ to phosphorylate the human clock proteins hPER1, hPER2 and hPER3. For example, HEK293T cells are co-transfected with hCKIε and Per1 or Per2. For the purpose of evaluating the relevancy of CKIε inhibition and CKIε inhibitors to circadian biology, a high-throughput cellular assay (33$^{rd}$ Annual Meeting, Soc. for Neurosci., Nov. 8-12, 2003, Abstract numbers 284.1, 284.2, and 284.3) was developed in which circadian rhythm could be monitored in a routine manner. The assay consists of Rat-1 fibroblasts stably expressing an Mper1-luc construct, thus enabling the determination of the rhythmic activation of the Mper1 promoter in living cells by repeatedly estimating luciferase activity by monitoring light-output over several days. The repeated measure format of the assay permits accurate and reproducible assessment of the concentration-dependent effects of CKIε inhibitors on circadian rhythm and provides the nexus for relating CKIε inhibition to circadian period alteration.

Sleep disorders have been classified into four major categories that include primary sleep disorders (dyssomnias and parasomnias), sleep disorders associated with medical/psychiatric disorders and a category of proposed sleep disorders for sleep disorders that cannot be classified due to insufficient data. Primary sleep disorders are thought to arise from abnormalities in the intrinsic systems responsible for sleep-wake generation (homeostatic system) or timing (circadian system). Dyssomnias are disorders in initiating or maintaining sleep and include primary insomnia, hypersomnia (excessive sleepiness), narcolepsy, breathing-related sleep disorder, circadian rhythm sleep disorder, and dyssomnias not otherwise specified. Primary insomnia is characterized by the persistence (>1 month) in difficulty of initiating and maintaining sleep or of non-restorative sleep. Difficulties in sleeping associated with primary insomnia leads to significant distress or impairment, including daytime irritability, loss of attention and concentration, fatigue and malaise, and deterioration of mood and motivation. Circadian rhythm sleep disorders include jet lag syndrome, shift work sleep disorder, advanced sleep phase syndrome and delayed sleep phase syndrome (J. Wagner, M. L. Wagner and W. A. Hening, Annals of Pharmacotherapy (1998) 32, 680-691). Individuals in a forced sleep paradigm demonstrate a greater wakefulness, as a percentage of sleep time, at certain periods of circadian day (Dijk and Lockley, J. Appl. Physiol. (2002) 92, 852-862). It has been generally accepted that with age there is an advance in our circadian rhythm for sleep and often results in less quality sleep (Am J Physiol Endocrinol Metab. (2002) 282, E297-E303). Thus, sleep occurring out of circadian phase may suffer in qualitative and quantitative terms, as further exemplified by alterations in sleep with shift work and jet lag. Disturbance of the human circadian clock can cause sleep disorders and agents that modulate circadian rhythmicity, such as an inhibitor of CKIε and/or CKIδ, may be useful for the treatment of sleep disorders, and particularly circadian rhythm sleep disorders.

Mood disorders are divided into depressive disorders ("unipolar depression"), bipolar disorders, and two disorders based on etiology that include mood disorder due to a general medical condition and substance-induced mood disorder. Depressive disorders are subclassified as major depressive disorder, dysthymic disorder and depressive disorder not otherwise specified. Bipolar disorders are subclassified as bipolar I disorder and bipolar II disorder. It has been observed that the specifier "seasonal pattern" can be applied to major depressive disorders that are recurrent and to the pattern of major depressive episodes in bipolar I disorder and bipolar II disorder. Prominent anergy, hypersomnia, overeating, weight gain, and a craving for carbohydrates often characterize major depressive episodes that occur in a seasonal pattern. It is unclear whether a seasonal pattern is more likely in major depressive disorder that is recurrent or in bipolar disorders. However, within the bipolar disorders, a seasonal pattern appears to be more likely in bipolar II disorder than in bipolar I disorder. In some individuals the onset of manic or hypomanic episodes may also be linked to a particular season. The winter-type seasonal pattern appears to vary with latitude, age and sex. Prevalence increases with higher latitudes, younger persons are at higher risk for winter depressive episodes, and females comprise 60% to 90% of persons with seasonal pattern. Seasonal affective disorder (SAD), a term commonly used in the literature, is a subtype of mood disorder that in the Diagnostic and Statistical Manual of Mental Disorders IV (DSM-IV) (American Psychiatric Association: "Diagnostic and Statistical Manual of Mental Disorders", Fourth Edition, Text Revision. Washington, DC, American Psychiatric Association, 2000) is denoted by the term "with seasonal pattern" when describing a seasonal pattern of major depressive episodes in bipolar I disorder, bipolar II disorder or recurrent major depressive disorder (E. M. Tam et al., Can. J. Psychiatry (1995) 40, 457-466). The characteristics and diagnoses of depressive disorders, major depressive disorder, major depressive episode, bipolar I disorder, bipolar II disorder and seasonal effects are described in DSM-IV.

Patients suffering from major depressive disorders, including SAD that is characterized by recurrent depressive episodes typically in winter, have been shown to be positively responsive to light therapy (Kripke, Journal of Affective Disorders (1998) 49(2), 109-117). The success of bright light treatment for patients with SAD and major depression resulted in the proposal of several hypotheses to explain the underlying mechanism of action for the therapeutic effect of light. These hypotheses included the "circadian rhythm hypothesis" that suggests the antidepressant effect of bright light could be associated with phase-shifting the circadian pacemaker relative to sleep (E. M. Tam et al., Can. J. Psychiatry (1995) 40, 457-466). In support of the link between light therapy and circadian rhythm, clinically effective light therapy in major depressive disorders causes a concomitant shift in circadian phase and the clinical effectiveness of light therapy appears to depend on the phase-shifting ability of the light therapy (Czeisler et al., The Journal of Physiology (2000) 526 (Part 3), 683-694; Terman et al., Arch. Gen. Psychiatry (2001) 58, 69-75). Additionally, light-therapy has been shown to accelerate and augment the effectiveness of the pharmacological treatment of major depressive disorders (Benedetti et al., J. Clin. Psychiatry (2003) 64, 648-653). Thus, inhibition of casein kinase Iε and/or casein kinase Iδ would be expected to cause a circadian phase shift and such inhibition represents a potential clinically effective mono- or combined therapy for mood disorders.

It should be noted that sleep disturbance is a criterion symptom for many psychiatric disorders (W. V. McCall, J. Clin. Psychiatry (2001) 62 (suppl 10), 27-32). Sleep disturbances are a common feature of depressive disorders and insomnia is the sleep disturbance that is frequently reported in depression, occurring in over 90% of depressed patients (M. E. Thase, J. Clin. Psychiatry (1999) 60 (suppl 17), 28-31). Accumulating evidence supports a common pathogenesis for primary insomnia and major depressive disorder. It has been hypothesized that corticotrophin releasing factor (CRF) hyperactivity (due to genetic predisposition or possibly early stress) and stress induce a process leading to exaggerated and protracted sleep disturbances, and eventually primary insomnia. Circadian rhythmicity in CRF secretion under non-stressed conditions may play a role in the normal sleep-wake expression (G. S. Richardson and T. Roth, J. Clin Psychiatry (2001) 62 (suppl 10), 39-45). Thus, agents that modulate circadian rhythmicity, for example by inhibition of casein kinase Iε and/or casein kinase Iδ, may be useful for treatment of depressive disorders due to effects on CRF secretion.

All of the references referred to hereinabove are incorporated herein in their entirety.

Thus it is an object of this invention to provide a series of substituted 1H-pyrrolo[3,2-b]pyridine-2-carboxamides, 1H-pyrrolo[3,2-c]pyridine-2-carboxamides and 1H-pyrrolo[2,3-c]pyridine-2-carboxamides that are inhibitors of casein kinase Iε. This object and other objects of this invention become apparent from the detailed discussion of the invention that follows.

SUMMARY OF THE INVENTION

The present invention provides substituted 1H-pyrrolo[3,2-b]pyridine-2-carboxamides, 1H-pyrrolo[3,2-c]pyridine-2-carboxamides, 1H-pyrrolo[2,3-c]pyridine-2-carboxamides and related analogs, and the pharmaceutically acceptable salts or stereoisomers thereof, of formula (I) as inhibitors of human casein kinase IF phosphorylation activity and to methods of using the compounds of formula (I) for the treatment of diseases and disorders of the central nervous system, such as for example mood disorders including major depressive disorder, bipolar I disorder and bipolar II disorder, and sleep disorders including circadian rhythm sleep disorders such as for example shift work sleep disorder, jet lag syndrome, advanced sleep phase syndrome and delayed sleep phase syndrome.

Accordingly, a broad embodiment of the invention is directed to a compound of formula (I)

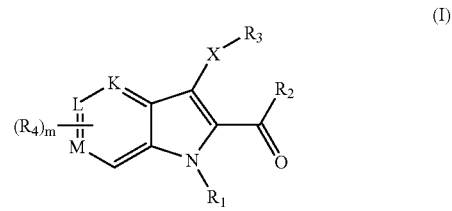

wherein:
$R^1$ is H or $C_{1-6}$alkyl;
$R_2$ is $NR_5R_6$;
$R_3$ is aryl or heterocycle;
$R_4$ is H, $C_{1-6}$alkyl, $C_{2-6}$-alkenyl, $C_{2-6}$-alkynyl, $C_{1-6}$alkoxy, $CF_3$, halogen, SH, S—$C_{1-6}$alkyl, $NO_2$, $NH_2$ or $NR_5R_6$;
$R_5$ is H or $C_{1-6}$alkyl;
$R_6$ is H or $C_{1-6}$alkyl;
X is S or $S(O)_n$;

one of K, L or M is N and the other two members of K, L or M are each C wherein $R_4$ is bonded only to a K, L, M or other ring atom that is C;

m is 1, 2 or 3; and n is 1 or 2;

or a pharmaceutically acceptable salt or a stereoisomer thereof.

One embodiment of the present invention relates to a pharmaceutical composition comprising a pharmaceutical carrier and a therapeutically effective amount of a compound of formula (I), or a pharmaceutically acceptable salt or stereoisomer thereof.

Another embodiment of the present invention relates a method of inhibiting casein kinase Iε by administering to a patient a therapeutically effective amount of a compound of formula (I).

Another embodiment of the present invention relates to a method of treating a patient suffering from a disease or disorder ameliorated by inhibition of casein kinase Iε that comprises administering to said patient a therapeutically effective amount of a compound of formula (I).

Another embodiment of the present invention relates to a process for preparing a compound of formula (I).

A further embodiment of the present invention relates to a compound of formula (I) prepared by a process of this invention as disclosed herein.

DETAILED DESCRIPTION OF THE INVENTION

As used herein, 'stereoisomer' is a general term used for all isomers of individual molecules that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers).

As used herein, 'R' and 'S' are used as commonly used in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counterclockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determining) group is on the right side of the carbon at the chiral center and 'L', that of the isomer in which it is on the left.

As used herein, "tautomer" or "tautomerism" refers to the coexistence of two (or more) compounds that differ from each other only in the position of one (or more) mobile atoms and in electron distribution, for example, keto-enol tautomers or tautomerism.

As used herein, "alkyl" means a saturated straight or branched chain aliphatic hydrocarbon group having from one to six carbon atoms, and includes methyl, ethyl, propyl, isopropyl, butyl, sec-butyl, tert-butyl and the like groups.

As used herein "alkenyl" means a linear or branched monovalent unsaturated aliphatic chain having from two to six carbon atoms and includes ethenyl (also known as vinyl), 1-methylethenyl, 1-methyl-1-propenyl, 1-butenyl, 1-hexenyl, 2-methyl-2-propenyl, 2,4-hexadienyl, 1-propenyl, 2-propenyl, 2-butenyl, 2-pentenyl, and the like groups.

As used herein "alkynyl" means a linear or branched monovalent unsaturated aliphatic having from two to six carbon atoms with at least one triple bond and includes ethynyl, 1-propynyl, 1-butynyl, 1-hexynyl, 2-propynyl, 2-butynyl, 2-pentynyl and the like groups.

As used herein, "alkoxy" means a monovalent substituent which consists of a straight or branched alkyl chain having from one to six carbon atoms linked through an ether oxygen atom and having its free valence bond from the ether oxygen, and includes methoxy, ethoxy, propoxy, isopropoxy, butoxy, sec-butoxy, tert-butoxy and the like groups.

As used herein the term $C_3$-$C_8$ cycloalkyl means a saturated hydrocarbon ring structure containing from three to eight carbon atoms and includes cyclopropyl, cyclobutyl, cyclopentyl, cyclohexyl, cycloheptyl, and the like.

As used herein, "aryl" or "Ar" means any stable monocyclic, bicyclic or tricyclic carbon ring of up to seven members in each ring, wherein at least one ring is aromatic and unsubstituted or substituted with from one to three substituents selected from the group consisting of methylenedioxy, hydroxy, $C_{1-6}$-alkoxy, halogen, $C_{1-6}$-alkyl, $C_{2-6}$-alkenyl, $C_{2-6}$-alkynyl, trifluoromethyl, trifluoromethoxy, —$NO_2$, —$NH_2$, —$NH(C_{1-6}$-alkyl), —$N(C_{1-6}$-alkyl)$_2$, —NH-acyl, and —$N(C_{1-6}$-alkyl)acyl. Examples of "aryl" or "Ar" include phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-trifluoromethylphenyl, 3-trifluoromethylphenyl, 4-trifluoromethylphenyl, 2-methoxyphenyl, 3-methoxyphenyl, 4-methoxyphenyl, 2-aminophenyl, 3-aminophenyl, 4-aminophenyl, 2-methylphenyl, 3-methylphenyl, 4-methylphenyl, 2-nitrophenyl, 3-nitrophenyl, 4-nitrophenyl, 2,4-dichlorophenyl, 2,3-dichlorophenyl, 3,5-dimethylphenyl, 2-trifluoromethoxyphenyl, 3-trifluoromethoxyphenyl, 4-trifluoromethoxyphenyl, naphthyl, tetrahydronaphthyl and biphenyl. The term "aryl-($C_1$-$C_6$-alkyl)" includes 2-methylphenyl, 3-methylphenyl, 4-methylphenyl, phenylmethyl (benzyl), phenylethyl, p-methoxybenzyl, p-fluorobenzyl and p-chlorobenzyl.

As used herein, the term "acyl" means both branched- and straight-chain saturated aliphatic hydrocarbon groups having the from one to six carbon atoms attached to a carbonyl moiety and includes acetyl, propionyl, butyryl, isobutyryl, and the like.

As used herein, "heterocycle" or "heterocyclic" means a stable 5- to 7-membered monocyclic or stable 8- to 11-membered bicyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. The heterocyclic ring may be unsubstituted or substituted with from one to three substituents selected from the group consisting of $C_{1-6}$-alkoxy, hydroxy, halogen, $C_{1-6}$-alkyl, $C_{2-6}$-alkenyl, $C_{2-6}$-alkynyl, trifluoromethyl, trifluoromethoxy, —$NO_2$, —$NH_2$, —$NH(C_{1-6}$-alkyl), —$N(C_{1-6}$-alkyl$)_2$, —NH-acyl, and —$N(C_{1-6}$-alkyl) acyl. Examples of such heterocyclic elements include piperidinyl, piperazinyl, 2-oxopiperazinyl, 2-oxopiperidinyl, 2-oxopyrrolidinyl, 2-oxoazepinyl, azepinyl, pyrrolyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoxazolyl, furyl, tetrahydrofuryl, benzofuranyl, tetrahydropyranyl, thienyl, benzothienyl, thiamorpholinyl, and oxadiazolyl.

As used herein, 'halogen', 'hal' or 'halo' means a member of the family of fluorine, chlorine, bromine or iodine.

When any variable (e.g., aryl, heterocycle, $R_1$, $R_2$, $R_3$, $R_4$, etc.) occurs more than one time in any constituent or in a compound of formula (I) of this invention, its definition on each occurrence is independent of its definition at every other occurrence. Also, combinations of substituents and/or variables are permissible only if such combinations result in stable compounds.

As used herein, 'treat', 'treating' or 'treatment' means:
(i) preventing a disease, disorder or condition from occurring in a patient that may be predisposed to the disease, disorder and/or condition, but has not yet been diagnosed as having it;
(ii) inhibiting a disease, disorder or condition, i.e., arresting its development; and
(iii) relieving a disease, disorder or condition, i.e., causing regression of the disease, disorder and/or condition.

As used herein, the term 'patient' means a warm blooded animal such as a mammal which is afflicted with a particular disease, disorder or condition. It is explicitly understood that guinea pigs, dogs, cats, rats, mice, horses, cattle, sheep, and humans are examples of animals within the scope of the meaning of the term.

As used herein, 'disease' means an illness, sickness or an interruption, cessation or disorder of body functions, systems or organs.

As used herein, 'disorder' means a disturbance of function, structure or both resulting from a genetic or embryologic failure in development, or from exogenous factors such as poison, injury or disease.

As used herein, 'condition' refers to a state of being, health or physical fitness.

As used herein, 'prophylaxis' means the prevention of disease.

As used herein, the term 'sleep disorder', 'sleep disorders' or 'sleep disturbance' means insomnia.

As used herein, the term 'insomnia' means the inability to sleep in the absence of external impediments, such as noise, bright light, etc., during the period when sleep should normally occur and the inability to sleep may vary in degree from restlessness or disturbed slumber to a curtailment of the normal length of sleep or to absolute wakefulness. The term 'insomnia' includes primary insomnia, insomnia related to a mental disorder, substance-induced insomnia and circadian rhythm insomnia that is insomnia due to a change in the normal sleep-wake schedule (shift changes, shift work sleep disorder, jet lag or jet lag syndrome, etc.).

As used herein the term 'primary insomnia' means difficulty in initiating sleep, in maintaining sleep or having restorative sleep which is not caused by a mental disorder or due to physiological effects of taking or withdrawing from certain substances (substance-induced insomnia).

As used herein the term 'circadian rhythm sleep disorder' includes jet lag or jet lag syndrome, shift work sleep disorder, advanced sleep phase syndrome and delayed sleep phase syndrome.

As used herein the term 'effective inhibitory amount of a compound' or 'effective casein kinase Iε inhibitory amount of a compound' means enough of a compound that becomes bioavailable through the appropriate route of administration to treat a patient afflicted with a disease, disorder or condition amenable to such treatment.

As used herein the term "a therapeutically effective amount" means an amount of a compound which is effective in treating the named disease, disorder or condition.

As used herein, the term 'pharmaceutically acceptable salt' is intended to apply to any salt, whether previously known or future discovered, that is used by one skilled in the art that is a non-toxic organic or inorganic addition salt which is suitable for use as a pharmaceutical. Illustrative bases which form suitable salts include alkali metal or alkaline-earth metal hydroxides such as sodium, potassium, calcium or magnesium hydroxides; ammonia and aliphatic, cyclic or aromatic amines such as methylamine, dimethylamine, triethylamine, diethylamine, isopropyldiethylamine, pyridine and picoline. Illustrative acids which form suitable salts include inorganic acids such as, for example, hydrochloric, hydrobromic, sulfuric, phosphoric and like acids, and organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids, and organic sulfonic acids such as methanesulfonic and p-toluenesulfonic acids.

As used herein, 'pharmaceutical carrier' refers to known pharmaceutical excipients useful in formulating pharmaceutically active compounds for administration, and which are substantially nontoxic and non-sensitizing under conditions of use. The exact proportion of these excipients is determined by the solubility and chemical properties of the active compound, the chosen route of administration as well as standard pharmaceutical practice. In practicing the methods of this invention, the active ingredient is preferably incorporated into a composition containing a pharmaceutical carrier, although the compounds are effective and can be administered, in and of themselves. That said, the proportion of active ingredient can vary from about 1% to about 90% by weight.

Further abbreviations that may appear in this application shall have the following meanings:

Me (methyl), Et (ethyl), Ph (phenyl), $Et_3N$ (triethylamine), p-TsOH (para-toluene sulfonic acid), TsCl (para-toluenesulfonyl chloride), hept (heptane), DMF (dimethylformamide), NMP (1-methyl-2-pyrrolidinone or N-methyl-2-pyrrolidinone), IPA (isopropanol or isopropyl alcohol), TFA (trifluoroacetic acid), DBU (1,8-diazabicyclo[5.4.0]undec-7-ene), DBN (1,5-diazabicyclo[4.3.0]non-5-ene), rt or r.t. (room temperature or ambient temperature), min or min. (minutes), h (hour or hours), UV (ultraviolet), LCMS (liquid chromatography mass spectrometry), t-Boc or Boc (tert-butoxycarbonyl), Bn (benzyl), t-Bu (tertiary butyl), i-Pr (isopropyl), HOAc (acetic acid), EtOAc (ethyl acetate), $Et_2O$ (diethylether), EtOH (ethanol), g (gram), mg (milligram), μg (microgram), ng (nanogram), mL (milliliter), μL (microliter), L (liter), HPLC (high-performance liquid chromatography), TLC, tlc or Tlc (thin layer chromatography), g/L (grams per liter), SiO$_2$ (silica gel), L/min (liters per minute), mL/min (milliliters per minute), mmol (millimole), M (molar), mM (millimolar), μM (micromolar), nM (nanomolar), μCi (microCurie), CPM (counts per minute), rpm (revolutions per minute), mm (millimeter), μm (micrometer), μ (micron), nm (nanometer), ppm (parts per million), psi (pounds per square inch), eq. or equiv. (equivalent), R$_T$ (retention time), ° C. (degrees Celsius), and K (Kelvin).

Accordingly, a broad embodiment of the invention is directed to a compound of formula (I)

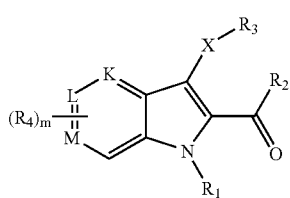

(I)

wherein R$_1$ is H or C$_{1-6}$alkyl; R$_2$ is NR$_5$R$_6$; R$_3$ is aryl or heterocycle; R$_4$ is H, C$_{1-6}$alkyl, C$_{2-6}$-alkenyl, C$_{2-6}$-alkynyl, C$_{1-6}$alkoxy, CF$_3$, halogen, SH, S—C$_{1-6}$alkyl, NO$_2$, NH$_2$ or NR$_5$R$_6$; R$_5$ is H or C$_{1-6}$alkyl; R$_6$ is H or C$_{1-6}$alkyl; X is S or S(O)$_n$; one of K, L or M is N and the other two members of K, L or M are each C wherein R$_4$ is bonded only to a K, L, M or other ring atom that is C; m is 1, 2 or 3; and n is 1 or 2.

One embodiment of this invention relates to compounds wherein L is N, and K and M are each C.

A further embodiment of this invention relates to compounds wherein L is N, K and M are each C, R$_1$, R$_4$, R$_5$ and R$_6$ is each H, and R$_3$ is aryl. The following compounds are representative examples within the scope of this embodiment:
3-phenylsulfanyl-1H-pyrrolo[3,2-c]pyridine-2-carboxylic acid amide,
3-(3-fluoro-phenylsulfanyl-1H-pyrrolo[3,2-c]pyridine-2-carboxylic acid amide and
3-(4-chloro-phenylsulfanyl-1H-pyrrolo[3,2-c]pyridine-2-carboxylic acid amide.

Another embodiment of this invention relates to compounds wherein M is N, and K and L are each C.

A further embodiment of this invention relates to compounds wherein M is N, K and L are each C, R$_1$, R$_4$, R$_5$ and R$_6$ is each H, and R$_3$ is aryl or heterocycle. The following compounds are representative examples within the scope of this embodiment:
3-phenylsulfanyl-1H-pyrrolo[2,3-c]pyridine-2-carboxylic acid amide,
3-(3-fluoro-phenylsulfanyl)-1H-pyrrolo[2,3-c]pyridine-2-carboxylic acid amide,
3-(3-methoxy-phenylsulfanyl)-1H-pyrrolo[2,3-c]pyridine-2-carboxylic acid amide,
3-(3-chloro-phenylsulfanyl)-1H-pyrrolo[2,3-c]pyridine-2-carboxylic acid amide,
3-(2-trifluoromethyl-phenylsulfanyl)-1H-pyrrolo[2,3-c]pyridine-2-carboxylic acid amide,
3-(2-trifluoromethoxy-phenylsulfanyl)-1H-pyrrolo[2,3-c]pyridine-2-carboxylic acid amide,
3-(2-methoxy-phenylsulfanyl)-1H-pyrrolo[2,3-c]pyridine-2-carboxylic acid amide, and
3-(pyridin-2-sulfanyl)-1H-pyrrolo[2,3-c]pyridine-2-carboxylic acid amide.

Another embodiment of this invention relates to compounds wherein K is N and L and M are each C.

A further embodiment of this invention relates to compounds wherein K is N, L and M are each C, R$_1$ is C$_{1-6}$alkyl, R$_5$ is H, R$_6$ is H or C$_{1-6}$alkyl, and R$_3$ is aryl. The following compounds are representative examples within the scope of this embodiment:
1-methyl-3-phenylsulfanyl-1H-pyrrolo[3,2-b]pyridine-2-carboxylic acid methylamide,
1-methyl-3-phenylsulfanyl-1H-pyrrolo[3,2-b]pyridine-2-carboxylic acid amide, and
3-phenylsulfanyl-1-propyl-1H-pyrrolo[3,2-b]pyridine-2-carboxylic acid amide.

A further embodiment of this invention relates to compounds wherein K is N, L and M are each C, R$_1$, R$_4$ and R$_5$ is each H, R$_3$ is aryl and R$_6$ is C$_{1-6}$alkyl. The following compounds are representative examples within the scope of this embodiment:
3-(3-trifluoromethyoxyphenylsulfanyl-1H-pyrrolo[3,2-b]pyridine-2-carboxylic acid methylamide,
3-(3-chlorophenylsulfanyl-1H-pyrrolo[3,2-b]pyridine-2-carboxylic acid methylamide,
3-(3-fluorophenylsulfanyl-1H-pyrrolo[3,2-b]pyridine-2-carboxylic acid methylamide, and
3-phenylsulfanyl-1H-pyrrolo[3,2-b]pyridine-2-carboxylic acid methylamide.

A further embodiment of this invention relates to compounds wherein K is N, L and M are each C, R$_1$, R$_4$, R$_5$ and R$_6$ is each H and R$_3$ is heterocycle. The following compounds are representative examples within the scope of this embodiment:
3-(quinolin-8-ylsulfanyl)-1H-pyrrolo[3,2-b]pyridine-2-carboxylic acid amide,
3-(pyridin-2-sulfanyl)-1H-pyrrolo[3,2-b]pyridine-2-carboxylic acid amide,
3-(pyridin-4-sulfanyl)-1H-pyrrolo[3,2-b]pyridine-2-carboxylic acid amide, and
3-(thiophen-2-ylsulfanyl)-1H-pyrrolo[3,2-b]pyridine-2-carboxylic acid amide.

A further embodiment of this invention relates to compounds wherein K is N, L and M are each C, R$_1$, R$_5$ and R$_6$ is each H and R$_3$ is aryl. The following compounds are representative examples within the scope of this embodiment:
3-phenylsulfanyl-1H-pyrrolo[3,2-b]pyridine-2-carboxylic acid amide,
3-(3-fluorophenylsulfanyl)-1H-pyrrolo[3,2-b]pyridine-2-carboxylic acid amide,
3-(3-chlorophenylsulfanyl)-1H-pyrrolo[3,2-b]pyridine-2-carboxylic acid amide,
3-(3-bromophenylsulfanyl)-1H-pyrrolo[3,2-b]pyridine-2-carboxylic acid amide,
3-(2-chlorophenylsulfanyl)-1H-pyrrolo[3,2-b]pyridine-2-carboxylic acid amide,
3-(4-chlorophenylsulfanyl)-1H-pyrrolo[3,2-b]pyridine-2-carboxylic acid amide,
3-(2,4-dichlorophenylsulfanyl)-1H-pyrrolo[3,2-b]pyridine-2-carboxylic acid amide,
3-(2-fluorophenylsulfanyl)-1H-pyrrolo[3,2-b]pyridine-2-carboxylic acid amide,
3-(2,3-dichlorophenylsulfanyl)-1H-pyrrolo[3,2-b]pyridine-2-carboxylic acid amide,
3-(2-trifluormethylphenylsulfanyl)-1H-pyrrolo[3,2-b]pyridine-2-carboxylic acid amide,
3-(3-trifluoromethyl-phenylsulfanyl)-1H-pyrrolo[3,2-b]pyridine-2-carboxylic acid amide,
3-(2-aminophenylsulfanyl)-1H-pyrrolo[3,2-b]pyridine-2-carboxylic acid amide,
3-(2,5-dichloro-phenylsulfanyl)-1H-pyrrolo[3,2-b]pyridine-2-carboxylic acid amide, 3-(2-methoxy-phenylsulfanyl)-1H-pyrrolo[3,2-b]pyridine-2-carboxylic acid amide, 3-(3-methoxy-phenylsulfanyl)-1H-pyrrolo[3,2-b]pyridine-2-carboxylic acid amide, 3-(3-amino-phenylsulfanyl)-1H-pyrrolo[3,2-b]pyridine-2-carboxylic acid amide, 3-(4-nitro-phenylsulfanyl)-1H-pyrrolo[3,2-b]pyridine-2-carboxylic acid amide, 3-(3-nitro-phenylsulfanyl)-1H-pyrrolo[3,2-b]pyridine-2-carboxylic acid amide, 3-o-tolylsulfanyl-1H-pyrrolo[3,2-b]pyridine-2-carboxylic acid amide, 3-p-tolylsulfanyl-1H-pyrrolo[3,2-b]pyridine-2-carboxylic acid amide, 3-(3,5-dimethyl-phenylsulfanyl)-1H-pyrrolo[3,2-b]pyridine-2-carboxylic acid amide, 3-m-tolylsulfanyl-1H-pyrrolo[3,2-b]pyridine-2-carboxylic acid amide, 3-(2-ethyl-phenylsulfanyl)-1H-pyrrolo[3,2-b]pyridine-2-carboxylic acid amide, 3-(3-trifluoromethoxy-phenylsulfanyl)-1H-pyrrolo[3,2-b]pyridine-2-carboxylic acid, amide, 3-(3-fluoro-phenylsulfanyl)-5-methoxy-1H-pyrrolo[3,2-b]pyridine-2-carboxylic acid amide, and 3-(3-methoxy-phenylsulfanyl)-5-methoxy-1H-pyrrolo[3,2-b]pyridine-2-carboxylic acid amide.

The compounds of the present invention can be prepared by processes analogous to those known in the art. Reaction schemes 1, 2 and 3, and the corresponding descriptive text, describe the preparation of the various compounds of the invention. The disclosed methods and examples are provided for illustration purposes and in no way limit the scope of the present invention. Alternative reagents, reaction conditions, and other combinations and permutations of the steps herein described to arrive at individual compounds are readily apparent to one of ordinary skill in the art. Tables 1, 2 and 3 provide summaries of the example compounds, and biological data for example compounds of the invention is summarized in Table 4.

CHEMICAL SYNTHESIS

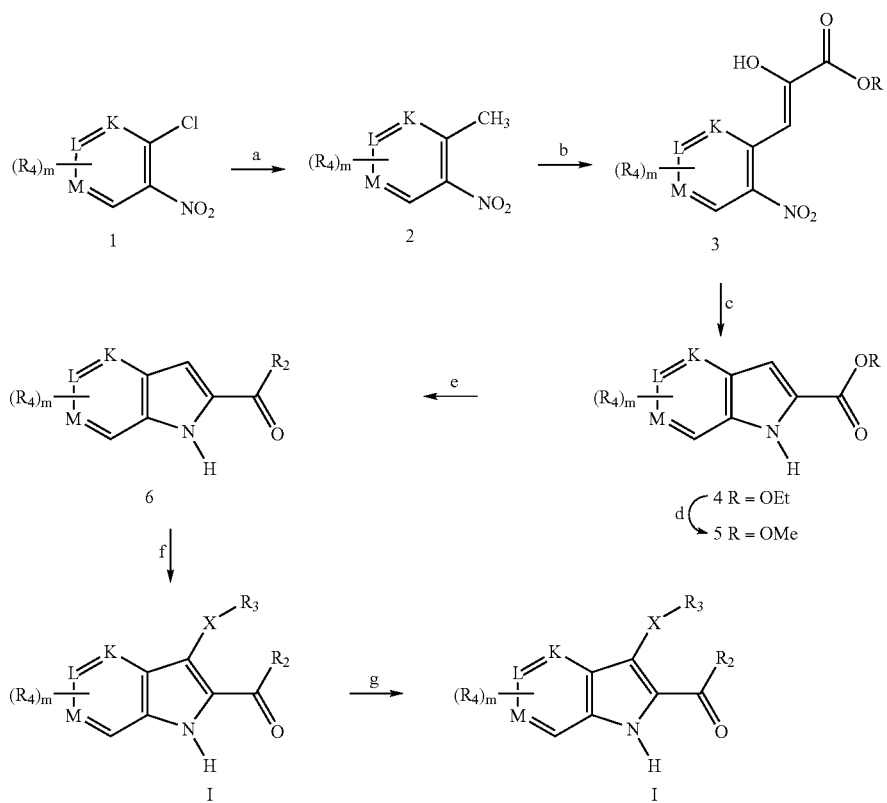

Scheme 1

Scheme 1 discloses a synthesis for the compounds of this invention from commercially available 2-chloro-3-nitropyridine (1a-1 wherein K is N and L and M are each C), 3-chloro-4-nitropyridine (1b-1 wherein L is N and K and M are each C) or 4-chloro-3-nitropyridine (1c-1 wherein M is N and K and L are each C), or an optionally substituted chloro-nitropyridine 1. The first digit of a compound number pertains to the corresponding compound or structure number as shown in any of Schemes 1-3, for example, the first digit 1 in 1a-1 pertains to compound or structure 1 in Scheme 1. The subsequent letter designation "a", "b" or "c" identifies a compound as a precursor for, or member of, the 1H-pyrrolo[3,2-b]pyridine-2-carboxamide series ("a", also known as 4-azaindole series), the 1H-pyrrolo[3,2-c]pyridine-2-carboxamide series ("b", also known as the 5-azaindole series) and the 1H-pyrrolo[2,3-c]pyridine-2-carboxamide series ("c", also known as the 6-azaindole series), respectively. The final digit or digits following the dash in a compound number identifies the specific compound in that structure series. Where a compound is only identified by a number, the number refers to the corresponding compound or structure as shown in any of Schemes 1-3, and it is understood that the discussion generically includes the three structural series as identified by "a", "b" and "c" as discussed above.

In Scheme 1, step a, chloro-nitropyridine 1 is added in portions to an alkali metal salt of a malonic acid diester in excess malonic diester, such as for example the sodium, potassium or lithium salt of the malonic acid diester in an excess of the malonic acid diester, such as for example diethyl malonate or dimethyl malonate, at a temperature of about 50° C. to about 70° C. The alkali metal salt of the malonic acid diester may be prepared, for example, by adding an alkali metal, such as for example sodium metal, to an excess of the malonic acid diester as is well known to one skilled in the art. After about three hours at about 50° C. to about 70° C., the mixture is allowed to stand at ambient temperature for about 12 to about 24 hours. If the reaction is incomplete, the mixture is heated to about 80° C. for about 2 hours to about 4 hours, then concentrated to remove excess malonic acid diester, and then treated with a concentrated mineral acid such as for example hydrochloric acid or sulfuric acid and water. The mixture is heated at about 100° C. to about 110° C. for about 5 hours to about 9 hours to effect decarboxylation. After standing about 12 to about 24 hours at ambient temperature the mixture is washed with a suitable solvent, such as for example ethyl ether and ethyl acetate, basified to about pH 8 to about pH 9 with an alkali metal hydroxide, such as for example sodium hydroxide or potassium hydroxide, and extracted with a suitable organic solvent, such as for example ethyl acetate. The organic extract is filtered and concentrated under reduced pressure to afford the desired methyl-nitropyridine 2. Preparation of 2 by this "step a" procedure is referred to as a "two step, one pot synthesis".

Alternatively, in Scheme 1, step a, methyl-nitropyridine 2 may be prepared by Suzuki coupling of 1 with methylboronic acid. Thus, a mixture of chloro-nitropyridine 1, methylboronic acid, potassium carbonate and tetrakis(triphenylphosphine)palladium(0) [Pd(PPh$_3$)$_4$] in a suitable aprotic solvent, such as for example dioxane, is heated at about 110° C. to about 120° C. for about 12 hours to about 16 hours. The reaction mixture is cooled to room temperature, concentrated and purified by chromatography to provide methyl-nitropyridine 2.

Advantageously it has now been found that compound 2 can also be prepared in one pot involving two steps in accordance with Scheme 1, step a. Accordingly, one adds to a polar solvent, such as for example dimethylformamide or N-methyl-2-pyrrolidinone, from about 2 to about 2.5 equivalents of a base, such as for example potassium t-butoxide, sodium ethoxide, sodium hydride, sodium t-butoxide, or sodium hexamethyldisilazide, at temperature of about 16° C. and with stirring for about 30 minutes. The mixture is then treated with about one to about four equivalents of a malonic acid diester, such as for example diethyl malonate, at a temperature of about 20° C. to about 35° C. After about 20 minutes, the mixture is treated at about 29° C. to about 44° C. with a solution of about one equivalent of compound 1 and a polar solvent such as for example dimethylformamide or N-methylpyrrolidone. The mixture is heated to about 50° C. until the reaction is complete as indicated by HPLC analysis or other chromatographic analysis as is well known to one skilled in the art. Most advantageously, compound 1 is condensed with about 2.0 equivalents of diethyl malonate wherein N-methyl-2-pyrrolidinone is the preferred solvent, wherein about 2.2 to about 2.5 equivalents of sodium t-butoxide is the preferred base, and wherein the above described order of additions, reaction temperatures and times are employed for this portion of the more advantageous "one pot, two step" (step a) synthesis of compound 2. When the reaction is complete, the mixture is treated with a mineral acid and water, preferably about 4.2 equivalents of 6M sulfuric acid, at about 100° C. for about 12 hours to effect decarboxylation. The reaction is quenched with ice water and extracted with a suitable solvent such as toluene to afford compound 2. The synthesis of compound 2a-1 (2-methyl-3-nitro-pyridine) by this advantageous "step a" procedure resulted in a surprisingly significant reduction in reaction time (about 2 hours versus about 3 days) for the condensation of 1a-1 with diethyl malonate, and provided 2a-1 in significantly improved overall yield (about 80% versus 30-68%) and significantly improved isolated purity (>96%) without the necessity of chromatographic purification. The method is advantageously reproducible with respect to yield and isolated purity. This procedure also advantageously avoids using sodium metal and relatively expensive reagents such as for example tetrakis(triphenyl-phosphine) palladium(0) that would be required for the preparation of compound 2 by other methods disclosed hereinabove.

As shown in Scheme 1, step b, 2-hydroxy-3-(nitro-pyridinyl)-acrylic acid ethyl ester 3 may be prepared by treating methyl-nitropyridine 2 with a suitable base, such as for example sodium ethoxide, lithium ethoxide, lithium t-butoxide, sodium t-butoxide, potassium t-butoxide or lithium hexamethyldisilazide, in a suitable solvent, such as for example ethanol or t-butanol, and then treating the reaction mixture with an oxalate diester such as for example dimethyl oxalate or diethyl oxalate at ambient temperature, and allowing the reaction mixture to stand for about 12 hours to about 48 hours at ambient temperature. The reaction mixture is then treated with a mineral acid, such as for example hydrochloric acid or sulfuric acid, to about pH 1. The precipitate is collected by filtration, washed sequentially with a suitable solvent, such as for example ethanol and di-isopropyl ether, respectively, to afford 2-hydroxy-3-(nitro-pyridinyl)-acrylic acid ethyl ester 3 or its tautomeric keto ester.

Advantageously it has been found that compound 3 may also be synthesized by another method according to Scheme 1, step b, by slowly adding compound 2 to a premixed solution of diethyl oxalate and a suitable base, in a suitable solvent, at about 2° C. to about ambient temperature. Accordingly a suitable base such as for example sodium ethoxide, lithium ethoxide, lithium t-butoxide, sodium t-butoxide, potassium t-butoxide or lithium hexamethyldisilazide is added to a suitable solvent such as for example tetrahydrofuran, at about 2° C. The mixture is stirred for about 20 minutes and then about 3 equivalents of diethyl oxalate is added at about −0.3° C. to about 4° C. After about 10 minutes, a solution of about one equivalent of compound 2 and a suitable solvent, such as for example tetrahydrofuran, is added at about 4° C. to about 9° C. The mixture is allowed to warm to ambient temperature. When the reaction is complete as indicated by HPLC analysis or other chromatographic analysis as is well known to one skilled in the art, the reaction mixture is cooled to about 1° C. and treated with saturated ammonium chloride solution at about 1° C. to about 9° C. Compound 3 is isolated by further dilution with water and/or a co-solvent, such as for example isopropanol. Most advantageously compound 2 is condensed with diethyl oxalate wherein sodium ethoxide is the preferred base and tetrahydrofuran is the preferred solvent following the above described order of additions, and reaction times and conditions. The synthesis of compound 3a-1 (2-hydroxy-3-(3-nitro-pyridin-2-yl)-acrylic acid ethyl ester) by this more advantageous "step b" procedure resulted in a surprisingly significant reduction in reaction time (about 2 hours versus about 2 to 3 days) and provided compound 3a-1 in significantly improved yield (about 88% versus 32-68%).

As shown in Scheme 1, step c, the desired 1H-pyrrolo[3,2-b]pyridine-2-carboxylic acid ester, 1H-pyrrolo[3,2-c]pyridine-2-carboxylic acid ester or 1H-pyrrolo[2,3-c]pyridine-2-carboxylic acid ester intermediates 4 may be prepared by catalytic or chemical reduction of the nitro group of an appropriately substituted 2-hydroxy-3-(nitro-pyridinyl)-acrylic acid ester 3, or its tautomeric keto ester, with concomitant pyrrole ring formation to afford compound 4. Thus, a mixture of compound 3 and a suitable catalyst, such as for example palladium on carbon, in a suitable solvent, such as for example ethanol or methanol, is hydrogenated in a manner as is well known to one skilled in the art for about one to about three hours at a pressure of about 45 psi to about 1200 psi to provide, after purification, intermediate compound 4. Advantageously compound 4 is prepared by this procedure wherein absolute ethanol is the preferred solvent and palladium on carbon is the preferred catalyst. Under these conditions, an advantageous low catalyst loading of 10 weight percent is achieved.

Alternatively, 2-hydroxy-3-(nitro-pyridinyl)-acrylic acid ethyl ester 3, or its tautomeric keto ester, may be chemically reduced to provide intermediate compound 4. For example a mixture of compound 3, $SnCl_2$ and $TiCl_4$ in a suitable solvent, such as for example ethanol, is heated at reflux for about 4 hours to provide, after purification by methods as are well known to one skilled in the art, intermediate compound 4.

When diethyl oxalate is employed for the preparation of compound 3, subsequent reduction of compound 3 affords intermediate compound 4 as the ethyl ester. Intermediate ethyl ester 4 may optionally be converted to other suitable esters by transesterification procedures as are well known to one skilled in the art. As shown in Scheme 1, step d, methyl ester 5 may be prepared by treating a methanol solution of ethyl ester 4 in the presence of a base, such as for example potassium carbonate or sodium carbonate, by heating the mixture at about 50° C. to about 80° C. for about one hour, or until the reaction is complete as determined by thin layer chromatography or other suitable chromatographic analysis as is well known to one skilled in the art. Dilution of the reaction with water and isolation of methyl ester 5 by filtration or extraction methods as are well known to one skilled in the art provides methyl ester 5.

As shown in Scheme 1, step e, intermediate esters 4 or 5 may be converted to amide 6 by methods well known to one skilled in the art. Thus, treating a solution of ester 4 or 5 in a suitable polar solvent, such as for example methanol or ethanol, with about 5N to about 7N ammonium hydroxide solution for about one day to about three days at ambient temperature, or by heating the solution to about 55° C. for about 10 hours, provides primary amide 6 after isolation by methods well known to one skilled in the art. Alternatively, ester 4 or 5 may be suspended in a mixture of concentrated ammonium hydroxide solution and lithium chloride at ambient temperature for about three to about five days until thin layer chromatographic analysis, or other suitable chromatographic analysis as is well known to one skilled in the art, indicates that the reaction is substantially complete. Amide 6 is isolated from the reaction mixture by methods well known to one skilled in the art. $N-C_{1-6}$-alkyl-substituted amides 6 are prepared by treating intermediate azaindole ester 4 or 5 with a $C_{1-6}$-alkyl amine by methods well known to one skilled in the art. For example, intermediate azaindole ester 4 or 5 may be treated with a $C_{1-6}$-alkyl amine, such as for example methylamine as a concentrated aqueous solution or neat with an excess of a $C_{1-6}$-alkyl amine, and monitoring the reaction for completion by thin layer chromatography or other chromatographic methods as are well known to one skilled in the art. The desired $N-C_{1-6}$-alkyl amide 6 is collected after dilution of the reaction with water or by extraction methods as are well known to one skilled in the art. Similar treatment of intermediate azaindole ester 4 or 5 with a $C_{1-6}$-dialkyl amine provides the corresponding $N-C_{1-6}$-dialkyl amide 6.

Advantageously, primary amide 6 is prepared according to Scheme 1, step e, by adding azaindole ethyl ester 4 to a solution of ammonia in methanol and heating under pressure until the reaction is complete. Use of methanol as solvent provides significantly greater solubility of the starting material and significantly faster reaction time. Azaindole ethyl ester 4 is also transesterified under these conditions to the corresponding azaindole methyl ester 5, but both esters 4 and 5 are converted to the desired primary amide 6 under the reaction conditions. The reaction is preferably conducted using 7N ammonia in methanol, a reaction temperature of about 50° C. and an initial pressure of about 35 psi for about 49 hours. During this time the pressure in the reaction vessel drops to about 16 psi. Completion of the reaction is determined by HPLC chromatographic analysis or other chromatographic analysis as is well known to one skilled in the art.

As shown in Scheme 1, step f, intermediate amide 6 is thioarylated at the 3-position of the pyrrole ring by methods well known to one skilled in the art. For example, a suspension of intermediate amide 6 in a suitable solvent, such as for example dimethylformamide or NMP, is treated with a suitable base, such as for example sodium hydride or lithium hydride, at ambient temperature, followed by treatment with a suitable diaryldisulfide, and then heating the mixture to about 90° C. to about 100° C. for about 12 hours to about 20 hours. The course of the reaction is followed by thin layer chromatographic analysis or other chromatographic methods as are well known to one skilled in the art. The reaction is then concentrated, diluted with water, and the desired compound of formula (I) is isolated and chromatographically purified by methods as are well known to one skilled in the art.

Alternatively, a mixture of intermediate amide 6 and about 1.5 equivalents of cesium carbonate in a suitable solvent, such as for example dimethylformamide or NMP, is treated with a suitable diarydisulfide (about 1.1 equivalents) and then the mixture is heated at about 90° C. to about 100° C. for about 12 hours to about 20 hours. The reaction is monitored by thin layer chromatography or other chromatographic methods as are well known to one skilled in the art. The compound of formula (I) is isolated and chromatographically purified by methods well known to one skilled in the art. Compounds of formula (I) wherein $R_3—X$ is heterocycle-S are prepared in a similar manner using appropriately substituted diheterocycledisulfides.

Advantageously, a compound of formula (I) is synthesized according to Scheme 1, step f, by adding to preferred solvent NMP as a single portion, about 1.5 equivalents of the diaryldisulfide, about two equivalents of cesium carbonate and about one equivalent of amide 6. The mixture is heated at about 120° C. for about 21 hours and the reaction is monitored by HPLC or other chromatographic methods are well known to one skilled in the art. If required to drive the reaction to completion, about 0.5 equivalent of cesium carbonate is optionally added, and heating is continued for about four hours. When complete as determined by chromatographic analysis, the reaction is cooled, quenched by pouring into water, and the desired compound of formula (I) is isolated and purified by methods well known to one skilled in the art. When a compound of formula (I) is prepared in this manner, the reaction time is surprisingly significantly shortened, and the compound of formula (I) is advantageously obtained in higher yield (85% versus 59%) and in sufficient purity such that further chromatographic purification of the product is unnecessary.

As shown in Scheme 1, step g, the nitrogen of the pyrrole ring of a compound of formula (I) may be N-alkylated by treating a solution of a compound of formula (I) wherein $R_1$ is H and a suitable solvent, such as for example 1,3-dimethyl-3,4,5,6-tetrahydro-2(1H)-pyrimidinone with a $C_{1-6}$-dialkyl-sulfate and a suitable base, such as for example cesium carbonate, at ambient temperature for about 12 hours to about 20 hours. Completion of the reaction is determined by thin layer chromatographic analysis or other chromatographic methods as are well known to one skilled in the art. When complete, the reaction mixture is diluted with water and the compound of formula (I) wherein $R_1$ is $C_{1-6}$-alkyl is isolated and purified by methods well known to one skilled in the art. The nitrogen of the pyrrole ring of a compound of formula (I) may also be alkylated by treating a pyridine solution of a compound of formula (I) wherein $R_1$ is H with a $C_1$-$C_6$-alkyl halide in the presence of a suitable base such as for example cesium carbonate with heating for about 0.25 hour to about 3 hours. The reaction mixture is cooled, diluted with water or concentrated to dryness, and extracted with ethyl acetate. Concentration and purification by chromatographic methods as are well known to one skilled in the art provides the compound of formula (I) wherein $R_1$ is $C_1$-$C_6$-alkyl. Other methods for N-alkylation of the pyrrole ring nitrogen of a compound of formula (I) wherein $R_1$ is H that are well known to one skilled in the art may be employed, for example by treatment of a compound of formula (I) wherein $R_1$ is H in a suitable polar solvent such as for example dimethylformamide or NMP, with a suitable base, such as for example sodium hydride or potassium t-butoxide, and then adding a $C_{1-6}$-alkyl halide such as for example, propyl iodide. Completion of the reaction is determined by thin layer chromatographic analysis or other chromatographic methods well known to one skilled in the art. When complete, the reaction mixture is diluted with water and the compound of formula (I) wherein $R_1$ is $C_{1-6}$-alkyl is isolated and purified by methods well known to one skilled in the art.

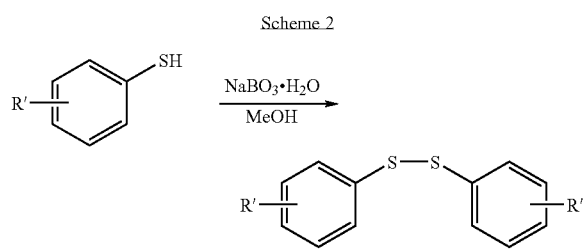

As shown in Scheme 2, diaryldisulfides are prepared by treating a solution of the appropriate arylsulfide in a suitable organic solvent, such as for example methanol, with an aqueous solution of sodium perborate and allowing the mixture to stand for about 12 to about 24 hours at ambient temperature. The diaryldisulfide may be isolated and purified by methods as are well known to one skilled in the art. Diheterocycledisulfides such as for example bis(2-thienyl)disulfide are prepared in a similar manner.

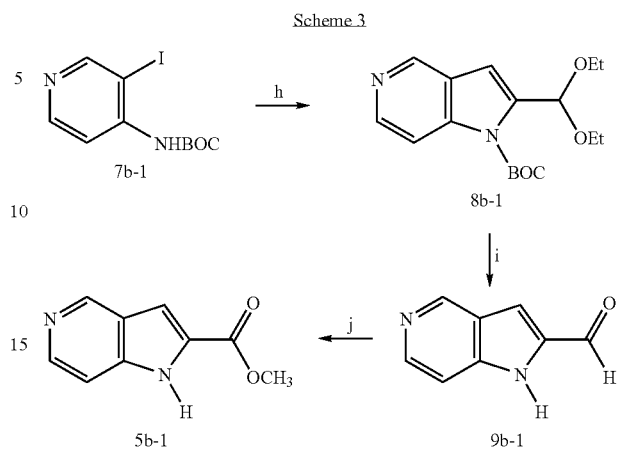

Scheme 3 discloses a synthesis of 1H-pyrrolo[3,2-c]pyridine-2-carboxylic acid methyl ester 5b-1. In Scheme 3, step h, a mixture of (3-iodo-pyridin-4-yl)carbamic acid 1,1-dimethylethyl ester (7b-1), 3,3-diethoxy-1-propyne, a base such as for example triethylamine or Hunig's base (N,N-diisopropylethylamine), dichlorobis(triphenylphosphine)palladium(II) and copper iodide is heated in a suitable solvent such as for example dry DMF under an inert atmosphere at about 90° C. for about three hours. The reaction mixture is cooled to about 70° C. and treated with a suitable base such as for example 1,8-diazabicyclo[5.4.0]undec-7-ene (DBU) or 1,5-diazabicyclo[4.3.0]non-5-ene (DBN), followed by stirring for about three hours at about 70° C. and then stirring at room temperature for about twelve hours. The reaction mixture is poured into ethyl acetate, washed with water and brine and the organic phase dried, filtered and concentrated to provide 2-(diethoxymethyl)-1H-pyrrolo[3,2-c]pyridine-1-carboxylic acid 1,1-dimethylethyl ester (8b-1) which is purified by chromatography or other methods as are well known to one skilled in the art. As shown in Scheme 3, step i, hydrolysis of compound 8b-1 is effected under acidic conditions to afford 1H-pyrrolo[3,2-c]pyridine-2-carboxaldehyde. Treatment of 8b-1 with a mineral acid such as for example hydrochloric acid for a suitable period of time such as about 20 hours at room temperature affords a mixture of 1H-pyrrolo[3,2-c]pyridine-2-carboxaldehyde (9b-1) and 2-formyl-1H-pyrrolo[3,2-c]pyridine-1-carboxylic acid 1,1-dimethylethyl ester after isolation and chromatographic separation of the product mixture by methods well known to one skilled in the art. Acidic hydrolysis of 2-formyl-1H-pyrrolo[3,2-c]pyridine-1-carboxylic acid 1,1-dimethylethyl ester by refluxing with a suitable acid such as for example trifluoroacetic acid and a suitable solvent such as for example dichloromethane affords 1H-pyrrolo[3,2-c]pyridine-2-carboxaldehyde, 9b-1. As shown in Scheme 3, step j, treatment of 1H-pyrrolo[3,2-c]pyridine-2-carboxaldehyde (9b-1) in a suitable solvent such as methanol with sodium cyanide and manganese dioxide with cooling at about 0° C. and stirring for about five hours provides 1H-pyrrolo[3,2-c]pyridine-2-carboxylic acid methyl ester 5b-1 after filtering, washing with water and isolation by methods as are well known to one skilled in the art.

All of the various embodiments of the compounds used in the methods of this invention as disclosed herein can be used in the method of treating various diseases and disorders as described herein. As stated herein the compounds used in the method of this invention are capable of inhibiting the effects of casein kinase Iε. One embodiment of this invention provides a method of treating a mood disorder and a sleep disorder. In another embodiment of the present invention the mood disorder may be a depressive disorder or a bipolar disorder. A further embodiment of the present invention relates to the treatment of a depressive disorder wherein the depressive disorder is major depressive disorder. Another embodiment of the present invention relates to the treatment of bipolar disorder wherein the bipolar disorder is bipolar I disorder or bipolar II disorder. Another embodiment of the present invention relates to the treatment of a sleep disorder. A further embodiment of the present invention relates to the treatment of a sleep disorder wherein the sleep disorder is a circadian rhythm sleep disorder. A further embodiment of the present invention relates to the treatment of a circadian rhythm sleep disorder wherein the circadian rhythm sleep disorder is shift work sleep disorder, jet lag syndrome, advanced sleep phase syndrome and delayed sleep phase syndrome. One skilled in the art readily appreciates that the diseases and disorders expressly stated herein are not intended to be limiting but rather to illustrate the efficacy of the compounds of the present invention. Thus, it is to be understood that the compounds of the invention may be used to treat any disease or disorder ameliorated by the inhibition of casein kinase Iε.

In another embodiment of the present invention, pharmaceutical compositions of the compounds of formula (I) of the invention are prepared in a manner well known to one skilled in the pharmaceutical arts. The carrier or excipients may be a solid, semisolid or liquid material which can serve as a vehicle or medium for the active ingredient. Suitable carriers or excipients are well known in the art. The pharmaceutical composition may be adapted for oral, inhalation, parenteral or topical use, and may be administered to the patient in the form of tablets, capsules, suspensions, syrups, aerosols, inhalants, suppositories, salves, powders, solutions and the like. As used herein, the term "pharmaceutical carrier" means one or more excipients. As described herein, the pharmaceutical compositions of the invention provide inhibition of casein kinase II and are thus useful for the treatment of diseases or disorders ameliorated by inhibition of casein kinase Iε

In preparing formulations of the compounds of the invention, care should be taken to ensure bioavailability of an effective amount of the active compound or compounds by the selected route, including oral, parenteral and subcutaneous routes. For example, effective routes of administration may include subcutaneously, intravenously, transdermally, intranasally, rectally, vaginally and the like including release from implants as well as injection of the active ingredient and/or composition directly into the tissue.

For oral administration, the compounds can be formulated into solid or liquid preparations, with or without inert diluents or edible carriers, such as capsules, pills, tablets, troches, powders, solutions, suspensions or emulsions. The capsules, pills, tablets, troches and the like may also contain one or more of the following adjuvants: binders such as microcrystalline cellulose, gum tragacanth; excipients such as starch or lactose, disintegrating agents such as alginic acid, corn starch and the like; lubricants such as stearic acid, magnesium stearate or Sterotex®, (Stokely-Van Camp Inc., Indianapolis, Ind.) glidants such as colloidal silicon dioxide; sweetening agents such as sucrose or saccharin; and flavoring agents such as peppermint, methyl salicylate or fruit flavoring. When the dosage unit form is a capsule, it may also contain a liquid carrier such as polyethylene glycol or a fatty oil. Materials used should be pharmaceutically pure and nontoxic in the amounts used. Alternatively, the pharmaceutical compositions may be prepared in a form suitable for extended release to provide a therapeutic amount of a compound of formula (I) of the invention in a suitable once daily, once weekly or once monthly form using methods as are will known to one skilled in the art. For example, an erodable polymer containing the active ingredient may be envisaged.

For parenteral administration, the compound may be administered as injectable dosages of a solution or suspension of the compound in a physiologically acceptable diluent with a pharmaceutical carrier which can be a sterile liquid such as water-in-oil or without the addition of a surfactant and other pharmaceutically acceptable excipients. Illustrative oils which can be employed in the preparations are those of petroleum, animal, vegetable or synthetic origin such as, for example, peanut oil, soybean oil and mineral oil. In general, water, saline, aqueous dextrose and related sugar solutions, ethanol and glycols, such as propylene glycol are preferred liquid carriers, particularly for injectable solutions. The parenteral preparation can be enclosed in ampoules, disposable syringes or multiple dose vials made of inert plastic or glass.

The solutions or suspensions described above may also include one or more of the following adjuvants: sterile diluents such as water for injection, saline solution, fixed oils, polyethylene glycols, glycerin, propylene glycol or other synthetic solvents, antibacterial agents such as ascorbic acid or sodium bisulfite; chelating agents such as ethylenediamine-tetra-acetic acid; buffers such as acetates, citrates or phosphates and agents for the adjustment of tonicity such as sodium chloride or dextrose.

The compounds can be administered in the form of a cutaneous patch, a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones. Suitable pharmaceutical carriers and formulation techniques are found in standard texts, such as *Remington: The Science and Practice of Pharmacy*, 19$^{th}$ edition, Volumes 1 and 2, 1995, Mack Publishing Co., Easton, Pa., U.S.A., which is herein incorporated by reference.

In the treatment of various disease states as described herein, a suitable dosage level is about 0.01 mg/kg per day to about 250 mg/kg per day, preferably about 0.05 mg/kg per day to about 100 mg/kg per day, and especially about 0.05 mg/kg per day to about 40 mg/kg per day. The compounds may be administered on a regimen of 1 to 4 times per day and as dictated by the nature of the disease or disorder to be treated.

EXAMPLES

The following examples are intended to serve for the illustration of the invention in greater detail, without restricting the breadth of the invention in any manner. Tables 1, 2 and 3 provide summaries of the example compounds that are prepared herein. Nitro compounds as described herein were handled with precaution due to perceived potential detonation liability of such compounds.

Unless otherwise noted, all starting materials, reagents and solvents were obtained from commercial suppliers and used without further purification. All reactions were run under inert atmosphere with dry reagents and solvents. Flash chromatography was carried out using EM Science silica gel 60

(40-63 mm) according to the literature using the solvent systems as described (Still, W. C.; Kahn, M.; Mitra, A. Rapid Chromatographic Technique for Preparative Separations with Moderate Resolution. J. Org. Chem., 1978, 43, 2923-2925). Thin layer chromatography was performed using 0.25 mm silica gel coated 60 F-254 plates (EM) and visualized using iodine vapor, UV light, or a staining reagent such as $KMnO_4$ solution (other staining solutions, when mentioned, were prepared as described in: "Thin-Layer Chromatography, A Laboratory Handbook", Egon Stahl, Ed.; Springer-Verlag Berlin-Heidelberg-New York, 1969).

Infrared (IR) spectra were recorded on a Nexus 670 FFIR (Nicolet) spectrometer with samples prepared as indicated, and are reported in wave numbers ($cm^{-1}$). $^1H$ NMR spectra were recorded on a Varian Gemini and/or mercury 300, Unity 400, or Unity plus and/or Inova 500 MHz spectrometers with chemical shifts (δ) reported in ppm relative to tetramethylsilane (0.0 ppm) or chloroform ($CDCl_3$, 7.26 ppm) as a reference. $^{13}C$ NMR spectra were recorded on a Varian Unity instrument (100.57 MHz, 13 C frequency) with chemical shifts (δ) reported in ppm relative to $CDCl_3$ (77.0 ppm), unless stated otherwise. Mass spectra (MS) were obtained on a Finnigan MAT Model TSQ 700 Mass Spectrometer System by chemical ionization at 120 eV using methane (CI, 120 eV). Liquid Chromatography Mass Spectrometry (LCMS) was performed on a Micromass LCT interfaced with a Gilson 215 liquid handler. High resolution mass spectrometric analysis (exact mass spectra) was performed in the ESI mode at mass resolution of 10,000 using a Micromass QTOF mass spectrometer. Exact mass values were determined for the protonated molecular ions (M+1) wherein M refers to the molecular ion.

Preparation of Pyrrolo[3,2-b]indoles (4-Azaindoles)

2-Methyl-3-nitro-pyridine, 2a-1 (Scheme 1, step a)

Add sodium metal (3.5 g) portion-wise over 1 hour to a 3 neck flask containing 79 mL of diethyl malonate heated to 90° C. under nitrogen. Lower the temperature to 60° C. and add 2-chloro-3-nitropyridine (1a-1, 25.0 g) portion-wise over 15 min. The reaction color turns to dark red. Keep the solution for 3 h at 60° C. and then allow to stand at rt overnight. Tlc indicates remaining starting material. Heat the solution to 80° C. for an additional 3 h (completion of the reaction). Remove the diethyl malonate under reduced pressure and take-up the dark brown residue in a mixture of conc. $H_2SO_4$ (18 mL) and $H_2O$ (32 mL). Heat the mixture for 7 h at 105° C. (decarboxylation) and then allow to stand at rt overnight. Wash the mixture with 3×150 mL of $Et_2O$ and 2×200 mL of EtOAc, and discard the washings. Basify the aqueous phase to pH 8-9 with NaOH and extract with 3×200 mL EtOAc. Filter the combined organic extracts over Celite® (diatomaceous earth) (Celite Corporation, 137 West Central Avenue, Lompor, Calif. 93436) and remove the solvent under reduced pressure. The residue crystallizes to give 2a-1 (15.0 g, 68%), mp 29-31° C.

2-Methyl-3-nitro-pyridine, 2a-1 (Scheme 1, step a)

Heat a mixture of 2-chloro-3-nitro-pyridine (1a-1, 7.9 g, 49.8 mmol), methylboronic acid (1.10 equiv. 54.8 mmol, 3.30 g), $K_2CO_3$ (3.0 equiv, 150 mmol, 20.7 g) and $Pd(PPh_3)_4$ (1.2 g, 1.2 mmol) to 110° C. in dioxane (250 mL) for 16 h. Allow the reaction to cool to rt, concentrate to a dark oil and flash chromatograph on $SiO_2$ (heptane/$Et_2O$ 3:1, dilute the oil with limited quantities of $CH_2Cl_2$ to apply to the column) to give compound 2a-1 (Niu, C.; Li, J.; Doyle, T. W.; Chen, S-H. Tetrahedron, 1998, 6311-6318).

2-Methyl-3-nitropyridine, 2a-1 (Scheme 1, step a)

Add NMP (2.0 L) to a 12-L, 3-neck flask fitted with a stirrer, a temperature probe and a reflux condenser fitted with a gas adapter for $N_2$ and cool to 16° C. Add sodium tert-butoxide (0.675 kg, 6.81 mol, 2.2 equiv., corrected for 97% purity) in one portion whereupon one observes an immediate exotherm to 29° C. Stir the mixture for 30 min to partially dissolve the NaOt-Bu and then add diethyl malonate (0.943 L, 6.19 mol, 2.0 equiv.) at 20° C. to 35° C. over 70 min with continual cooling whereupon a homogeneous solution forms. Stir for 20 min and add a solution of 2-chloro-3-nitropyridine (1a-1, 0.491 kg, 3.09 mol, 1.0 equiv.) and NMP (1.0 L) to the reaction mixture at 29° C. to 44° C. over 70 min. Heat the reaction mixture to 50° C. Monitor the progress of the reaction HPLC (Agilent series 1100; Waters Symmetry C8 (5μ) column (3.9×150 mm), flow rate at 1.0 mL/min. Isocratic: $CH_3CN$/0.1% aq. TFA, 50/50; λ=220 nm. $R_T$: diethyl malonate=2.6 min, 2-chloro-3-nitropyridine=2.7 min, 2-(3-nitro-pyridin-2-yl)-malonic acid diethyl ester =3.9 min). Typically >99% conversion occurs within 1-2 h. Discontinue heating and add 6M $H_2SO_4$ (2.17 L) at 50° C. to 59° C. over 45 min. A thick solid precipitate forms during the addition. Heat the mixture to 100° C. The evolution of gas occurs. Monitor the progress of the reaction by HPLC as previously described ($R_T$: 2-methyl-3-nitropyridine 2a-1=2.0 min, 2-(3-nitro-pyridin-2-yl)-malonic acid diethyl ester=3.9 min). Typically one observes >99% conversion within 12 h. Allow the mixture to cool to 40° C. and pour into ice water (20 kg, pH 1.5). Add 25% aq. NaOH (2.65 L) at −11° C. to −6° C. over 20 min to pH 11. Add toluene (4.0 L) and stir the mixture for 10 min. Filter the mixture through Celite® to remove inorganic solids and wash the filtercake with toluene (6.0 L). Separate the phases and extract the aqueous phase twice with toluene (6.0 L and 4.0 L). Filter the combined toluene phases through Celite® and wash the filter cake with toluene (1.0 L). Combine the toluene filtrates and wash with water (2×3.0 L). Dry ($MgSO_4$) the toluene phase, filter and concentrate to give 2-methyl-3-nitropyridine 2a-1 (0.34 kg, 80% yield, correct for residual NMP and toluene) as an oil. HPLC analysis shows the material to be 96% pure. $^1H$ NMR ($CDCl_3$) δ 2.87 (s, 3H), 7.35 (dd, 1H, J=4.8, 8.1 Hz), 8.27 (dd, 1H, J=1.4, 8.1 Hz), δ 8.72 (dd, 1H, J=1.4, 4.8 Hz).

2-Hydroxy-3-(3-nitro-pyridin-2-yl)-acrylic acid ethyl ester, 3a-1 (Scheme 1, step b)

Add to a 3 neck flask containing 500 mL of absolute ethanol under $N_2$, 2.2 g (0.0956 g-atom) of sodium. After all the sodium reacts, add diethyl oxalate (98 mL) dropwise, and then add compound 2a-1 (one equivalent). The color turns from light yellow to brown upon addition. Allow the resulting solution to stand for two days at rt. Treat the orange mixture with 5N HCl (pH=1), collect the precipitate by filtration and wash the filter cake with 100 mL EtOH and 200 mL diisopropyl ether to afford 3a-1 as 2-hydroxy-3-(3-nitro-pyridin-2-yl)-acrylic acid ethyl ester ($R_4$=H, 20 g, 86%) or its tautomeric ketoester or as a mixture of keto-enol tautomers. $^1H$ NMR (DMSO-$d_6$) δ 8.83 (dd, 1H, J=1.1, 5.0 Hz), 8.65 (dd, 1H, J=1.5, 8.4 Hz), 7.56 (dd, 1H, J=5.0, 8.4 Hz), 7.11 (s, 1H), 3.47 (bs, 1H), 4.28 (q, 2H, J=7.1 Hz), 1.30 (t, 3H, J=7.0 Hz).

2-Hydroxy-3-(3-nitro-pyridin-2-yl)-acrylic acid ethyl ester, 3a-1 (Scheme 1, step b)

Add tetrahydrofuran (2.7 L) to a 22-L, 3-neck flask fitted with a stirrer, temperature probe and an addition funnel fitted with a gas inlet adapter for $N_2$, and cool to about 2° C. Add sodium ethoxide (0.409 kg, 6.02 mol, 2.0 equiv.) in one portion. One observes a slight exotherm to 2.7° C. Stir the mixture for 20 min, add diethyl oxalate (1.22 L, 9.03 mol, 3.0 equiv.) at −0.34° C. over 50 min (slightly exothermic) and then stir the mixture for 10 min. Add a solution of 2-methyl-3-nitropyridine (2a-1, 0.415 kg, 3.01 mol, 1.0 equiv.) and THF (0.625 L) at 4-9° C. over 22 min without cooling. Allow the mixture to warm to rt over 1 h. Monitor progress of the reaction by HPLC (Agilent series 1100 using the following conditions: Waters Symmetry C8 (5μ) column (3.9×150 mm), flow rate at 1.0 mL/min; $CH_3CN/0.1\%$ aq. TFA, 55/45; λ=210 nm; $R_T$: 2-methyl-3-nitropyridine 2a-1=1.8 min, 3a-1=2.7 min). Typically one observes >99% conversion to product within 2-3 h. During the reaction, a thick red precipitate forms. Cool the reaction mixture to about 1° C. and add saturated $NH_4Cl$ solution (2.0 L) at 1° C. to 9° C. Add water (5.9 L) (pH 7.4) and then add IPA (3.5 L). Stir the mixture for 1 h and collect the red colored solid by filtration. Wash the filter cake with $IPA/H_2O$ (1:4, 8.0 L), $H_2O$ (15 L) and air dry. Dry the filter cake (40° C./0.1 in Hg) to give 3a-1 (0.635 kg, 89%). $^1$H NMR ($CDCl_3$) δ 1.40 (t, 3H, J=7 Hz), 4.38 (q, 2H, J=7 Hz), 7.36 (m, 2H), 8.42 (dd, 1H J=1.5, 8.4 Hz), 8.66 (dd, 1H, J=1.5, 4.8 Hz), 14.52 (2, 1H, OH).

1H-Pyrrolo[3,2-b]pyridine-2-carboxylic acid ethyl ester, 4a-1 (Scheme 1, step c)

Hydrogenate 3a-1 (20 g) over 10% palladium on carbon (5.5 g) in EtOH (350 mL) at rt for 3 hours under 1200 psi. Filter the reaction mixture through Celite® and concentrate the filtrate to give ester 4a-1 ($R_4$=H) in 39% yield.

Alternatively, reduce 3a-1 with $SnCl_2$ (5.0 equiv), $TiCl_4$ (2.5 equiv) in EtOH at reflux for 4 h, cool to ambient temperature, concentrate and purify by silica gel chromatography to provide ester 4a-1 ($R_4$=H) in 81% yield. $^1$H NMR (DMSO-$d_6$) δ 13.48 (bs, 1H), 8.80 (dd, 1H, J=0.7, 5.4 Hz), 8.56 (dd, 1H, J=0.7, 8.4 Hz), 7.80 (dd, 1H, J=5.5, 8.4 Hz), 7.37 (s, 1H), 4.40 (q, 2H, J=7.0 Hz), 1.38 (t, 3H, J=7.0 Hz).

1H-Pyrrolo[3,2-b]pyridine-2-carboxylic acid ethyl ester, 4a-1 (Scheme 1, step c)

Add to a 2 L thick-walled Parr reactor compound 3a-1 (56.8 g, 0.24 mol), ethanol (200 proof, 850 mL, 15 parts) and 10% Pd/C (5.7 g, 10% by wt.). Connect the reaction vessel to a Parr hydrogenator, flush with hydrogen and pressurize the orange slurry to 45 psi. Shake at rt for 1 h during which time the temperature rises to 57° C. When the temperature of the reaction mixture stabilizes at 35° C., slowly heat the reaction to 40° C. for 3 h. When the reaction is complete as determined by-TLC (silica gel, 1% MeOH in $CH_2Cl_2$), cool the reaction mixture to rt, filter the slurry through Celite®, and wash the filter cake with EtOH (4×200 mL). Concentrate the yellow filtrate to afford a solid (41.6 g), add ethyl acetate (302 mL) and heat on a steam bath. Cool the mixture to rt and add heptane (600 mL) to precipitate the product. Stir the mixture in an ice bath for 1 h, filter and wash the filter cake with heptane (100 mL). Dry the filter cake (50° C./0.1 in Hg) for 24 h to give 4a-1 as a light gray solid (36.6 g, 81% yield). $^1$H NMR (DMSO-$d_6$) 1.36 (t, 3H, J=7.0 Hz), 4.36 (q, 2H, J=7.0 Hz), 7.19 (s, 1H), 7.25 (dd, 1H, J=4.5, 8.1 Hz), 7.82 (d, 1H, J=8.1 Hz), 8.44 (d, 1H, J=4.5 Hz), δ 12.11 (s, 1H).

1H-Pyrrolo[3,2-b]pyridine-2-carboxylic acid amide, 6a-1 (Scheme 1, step e)

Dissolve ester 4a-1 in 5N ammonia solution in MeOH and heat to 55° C. for 10 h to give, after work-up, amide 6a-1 ($R_2$=$NH_2$, $R_4$=H) in 44% yield, mp 332° C. (dec.). $^1$H NMR (DMSO-$d_6$) δ 11.72 (bs, 1H), 8.36 (dd, 1H, J=1.5, 4.5 Hz), 8.10 (bs, 1H), 7.76 (dd, 1H, J=2.2, 8.2 Hz), 7.52 (bs, 1H), 7.24 (s, 1H), 7.17 (dd, 1H, J=4.5, 8.2 Hz).

1H-Pyrrolo[3,2-b]pyridine-2-carboxylic acid amide, 6a-1 (Scheme 1, step e)

Dissolve ester 4a-1 in 7N ammonia solution in MeOH and stir at rt for several days monitoring by tlc (10% MeOH/$CH_2Cl_2$). When complete, concentrate the reaction to minimum volume, dilute with excess $H_2O$, collect the precipitate by filtration, and dry to give amide 6a-1 ($R_2$=$NH_2$, $R_4$=H) in about quantitative yield.

1H-Pyrrolo[3,2-b]pyridine-2-carboxylic acid amide, 6a-1 (Scheme 1, step e)

Suspend ester 4a-1 in concentrated $NH_4OH$ and stir at rt for several days monitoring by tlc (10% MeOH/$CH_2Cl_2$). When complete, concentrate the reaction to minimum volume, dilute with excess $H_2O$, collect the precipitate by filtration and dry to give amide 6a-1 ($R_2$=$NH_2$, $R_4$=H) in about quantitative yield.

1H-Pyrrolo[3,2-b]pyridine-2-carboxylic acid amide, 6a-1 (Scheme 1, step e)

Add a solution of 7 N $NH_3$ in MeOH (1.5 L, 10.5 mol, 20 equiv.) to a 3-L pressure reactor at rt and then add azaindole ester 4a-1 (100 g, 0.53 mol) as a solid. Slowly heat the slurry to 50° C. to afford a clear solution. One observes the initial pressure of 35 psi to drop to 16 psi over 4 h. Maintain the reaction at 50° C. for 49 h. One observes a final pressure of 10 psi. Monitor the progress of the reaction by HPLC (Agilent series 1100 using the following conditions: Waters Symmetry C8 (5μ) column (3.9×150 mm), flow rate at 1.0 mL/min, gradient elution conditions: time (minutes), water:acetonitrile-methanol ratio (acetonitrile-methanol used as a 1:1 solution) 0 min., 70:30; 10 min., 20:80; 15 min., 70:30; 20 min., 70:30; $\lambda_1$=210 nm, $\lambda_2$=220 nm, flow rate 1.0 mL/min, $R_T$: ethyl ester 4a-1=5.6 min, methyl ester 5a-1=4.2 min, amide 6a-1=2.2 min). One observes the corresponding methyl ester 5a-1 being formed in the reaction and 5a-1 serves also as an intermediate in the reaction. Cool the reaction to 4° C. and isolate the resulting precipitate by vacuum filtration. Wash the filter cake with methyl tert-butyl ether (2×100 mL) and dry (40° C./0.1 in Hg) for 20 h to give 6a-1 as a gray solid (78.6 g, 93%). $^1$H NMR (DMSO-$d_6$) δ 7.17 (dd, 1H, J=4.5, 8.4 Hz), 7.53, 8.11 (2s, 2H, $NH_2$), 7.76 (d, 1H, J=8.1 Hz), 8.37 (d, 1H, J=1.5 Hz), 11.72 (s, 1H, NH).

1H-Pyrrolo[3,2-b]pyridine-2-carboxylic acid methylamide, 6a-2

Stir 4-azaindole ester 4a-1 (R=Et, $R_4$=H) neat in methylamine (40 wt % solution in $H_2O$) at rt for 16 h monitoring by tlc (10% MeOH/$CH_2Cl_2$). When complete, dilute the reaction excess $H_2O$, collect the precipitate by filtration and dry to provide 6a-2 ($R_2$=$NHCH_3$, $R_4$=H) as an ivory colored solid (see General Synthetic procedure VI). MS Obs 176.07 (M+1).

General Preparation of Diaryldisulfide and Diheterocycledisulfide Starting Materials (Scheme 2)

Add to a solution of the unsubstituted or appropriately substituted phenylthiol (17.2 millimole, 1.0 equivalent) and MeOH (30 mL), a solution of sodium perborate (22 millimole) and water (20 mL) with stirring, and then allow the reaction to stand at rt overnight. Collect the solid by filtration and wash with methanol to give the desired diaryldisulfide. Other disulfides including diheterocycledisulfides (e.g. bis(2-thienyl)disulfide) can be prepared in a similar manner as described for the preparation of the desired diaryldisulfides.

General Synthetic Procedure I (Transesterification, Scheme 1, Step d)

Add to ethyl 4-azaindole-2-carboxylate 4a (42.3 mmol) in MeOH (50 mL), $K_2CO_3$ (1.20 equiv, 50.7 mmol) and stir the suspension with heating to 55° C. for 1 h. Monitor the reaction by tlc (Et$_2$O/hept). When complete, concentrate the reaction in vacuo, dilute with H$_2$O and stir for 15 min. Collect the solid by filtration and dry in a vacuum oven at 65° C. for 3 h to afford about 90% to about 100% of the desired methyl 4-aza-indole-2-carboxylate 5a.

General Synthetic Procedure II (Amidation Using NH$_4$OH, Scheme 1, Step e)

Stir 4-azaindole carboxylate ester 4a or 5a (40.0 mmol) as a suspension in concentrated NH$_4$OH (100 mL) and LiCl (1.0 equiv) at rt for 16 h. Collect the ivory colored solid by filtration, wash with H$_2$O and air dry to give primary amide 6a (60-75%).

General Synthetic Procedure III (Amidation using NH$_3$/MeOH, Scheme 1, Step e)

Stir ethyl 4-aza-2-indole carboxylate 4a (4.67 mmol) in 7N NH$_3$/MeOH (20 mL) and add LiCl (1.0 equiv, 4.67 mmol). Stir the reaction at rt for 5 days monitoring by tlc (10% MeOH/CH$_2$Cl$_2$) during which time a precipitate forms. Concentrate the mixture to minimum volume, dilute with H$_2$O and collect the solid by filtration. Wash the filter cake with H$_2$O and dry under vacuum at 60° C. to afford primary amide 6a (>90%).

General Synthetic Procedure IVa (3-thioarylation Using NaH as Base, Scheme 1, Step f)

To a stirred suspension of NaH (60% oil dispersion, 1.2 equiv, 9.8 mmol) in DMF (75 mL) under N$_2$ at rt add 4-aza-indole-2-carboxyamide 6a (8.18 mmol) as a solution in DMF (5 mL). After 5 min. add the diaryldisulfide (1.0 equiv., 8.18 mmol) in one portion and then heat the reaction with stirring to 95° C. for 16 h. Follow the reaction by partitioning an aliquot of the reaction mixture between EtOAc/H$_2$O and monitor by tlc (10% MeOH/CH$_2$Cl$_2$). When complete, concentrate the reaction mixture in vacuo, dilute with H$_2$O, stir for 30 min, filter and air-dry the filter cake. Chromatograph the crude solid on SiO$_2$ eluting with 9:1 CH$_2$Cl$_2$/MeOH to provide 3-arylthioether 1a (R$_1$=H).

General Synthetic Procedure IVb (3-thioarylation Using Cs$_2$CO$_3$, Scheme 1, Step f)

To 4-aza-indole-2-carboxyamide 6a (0.42 mmol) dissolved in dry DMF (10 mL) add Cs$_2$CO$_3$ (100 mg, 0.31 mmol) and then add the diaryldisulfide (1.1 equiv., 0.46 mmol). Heat the reaction under N$_2$ at 95° C. for 16 h (monitor by tlc/LCMS for completion). Allow the reaction to cool to rt, and then pour with stirring into ice-cooled H$_2$O. Collect the precipitate by filtration and dry in a vacuum oven at 40° C. to provide the crude product as a tan crystalline solid. Purification by chromatography on SiO$_2$ provides 3-arylthioether 1a (R$_1$=H).

General Synthetic Procedure V (Pyrrole Ring N-methylation, Scheme 1, Step g)

Add with stirring to 3-substituted-4-azaindole-2-carboxylic acid amide Ia (R$_1$=H, 0.24 mmol) and 1,3-dimethyl-3,4,5,6-tetrahydro-2(1H)-pyrimidinone (5.0 mL), dimethylsulfate (1.5 equiv, 0.36 mmol) and Cs$_2$CO$_3$ (2.0 equiv, 0.48 mmol). Stir the reaction at rt for 16 h monitoring by tlc (10% MeOH(CH$_2$Cl$_2$). When complete, concentrate the reaction mixture to minimum volume, dilute with H$_2$O and collect the precipitate by filtration. Wash the filter cake with additional H$_2$O and dry under vacuum at 40° C. to afford 1-methyl-3-substituted-4-azaindole-2-carboxylic acid amide Ia (R$_1$=CH$_3$, 65%).

Other methods for N-alkylation of the pyrrole ring nitrogen of a compound of formula (I) that are well known to one skilled in the art may be employed. For example, by treatment of a compound of formula (I) wherein R$_1$ is H in a suitable polar solvent, such as for example dimethylformamide or NMP, with a suitable base, such as for example sodium hydride or potassium t-butoxide, and then adding an alkyl halide, such as for example propyl iodide, provides the compound of formula (I) wherein R$_1$ is propyl.

General Synthetic Procedure VI: General Preparation of the Indole-2-methylamide and Other Secondary Amides (Scheme 1, Step e)

Stir 4-azaindole ester 4 or 5 with a C$_{1-6}$alkylamine (e.g. methyl amine 40 wt % solution in H$_2$O or neat) at rt for 16 h monitoring by tlc (10% MeOH(CH$_2$Cl$_2$). When complete, dilute the reaction with excess H$_2$O, collect the solid precipitate by filtration and dry to give secondary amide 6 (R$_2$=NH—C$_{1-6}$alkyl) in about quantitative yield.

3-Phenylsulfanyl-1H-pyrrolo[3,2-b]pyridine-2-carboxylic acid amide, Ia-1.

Add to 1H-pyrrolo[3,2-b]pyridine-2-carboxylic acid amide (6a-1, R$_4$=H; 1.0 equiv) in DMF (100 mL), diphenyldisulfide (1.0 equiv) as described in General Synthetic Procedure IVb to provide Ia-1 as a tan crystalline solid (81%), mp 251° C., tlc R$_f$=0.49. $^1$H NMR (DMSO-d$_6$) δ 12.48 (bs, 1H), 8.45 (dd, 1H, J=1.5, 4.4 Hz), 8.11 (bs, 1H), 7.89 (dd, 1H, J=1.5, 4.0 Hz overlapping with a bs, 1H), 7.31 (dd, 1H, J=1.4, 4.5 Hz), 7.28 (dd, J=1.5, 4.5 Hz, 1H) 7.21 (m, 2H), 7.13-7.05 (m, 3H); m/z=270.06 (M+H). Anal. Calcd. For C$_{14}$H$_{11}$N$_3$SO: C, 62.44; H, 4.12; N, 15.6. Found: C, 62.31; H, 4.08; N, 15.39.

3-Phenylsulfanyl-1H-pyrrolo[3,2-b]pyridine-2-carboxylic acid amide, Ia-1 using excess Cs$_2$CO$_3$ Add NMP (1.20 L) to a 3-L 3-neck flask fitted with a mechanical stirrer, a temperature probe and a reflux condenser under nitrogen. Add in one portion diphenyldisulfide (177.8 g, 1.5 equiv.), Cs$_2$CO$_3$ (351.9 g, 2.0 equiv.) and amide 6a-1 (87.5 g, 0.54 mol). Heat the reaction mixture at 120° C. for 21 h. Monitor the progress of the reaction by HPLC (Agilent series 1100 using the following conditions: Waters Symmetry C8 (5μ) column (3.9×150 mm), flow rate at 1.0 mL/min, gradient elution conditions: time (minutes), water: acetonitrile-methanol ratio (acetonitrile-methanol used as a 1:1 solution) 0 min., 70:30; 10 min., 30:70; 15 min., 30:70; 20 min., 70:30; 25 min., 70:30; λ$_1$=210 nm, λ$_2$=300 nm, flow rate: 1.0 mL/min. (R$_T$: amide 6a-1=2.1 min, product Ia-1=5.7 min, PhSSPh=14.0 min, NMP=1.9 min). If the reaction is not complete, add additional Cs$_2$CO$_3$ (87.97 g, 0.5 equiv.) and maintain the reaction at 120° C. for another 4 h. Cool the reaction mixture to rt, pour into ice water and stir for 1 h. Collect the brown colored solid by filtration, wash the filter cake twice with water and air-dry for 6 h. Slurry the solid twice with 20% EtOAc/heptane at rt to remove PhSSPh. Decolorize the crude product in THF with charcoal at reflux for 1 h, filter and work-up to give Ia-1 as a light brown solid. Slurry Ia-1 in ethanol (12 parts), reflux for one hour, and cool in an ice bath with stirring. Collect the solid by filtration, wash with cold EtOH and dry (40° C./0.1 in Hg) to give Ia-1. $^1$H NMR (DMSO-d$_6$) δ 7.05-7.32 (m, 6H), 7.91 (m, 2H), 8.12 (s, 1H, NH$_2$), 8.45 (dd, 1H, J=4.5, 0.9 Hz), 12.50 (s, 1H, NH). Analysis: Calculated for C$_{12}$H$_{11}$N$_3$OS: 62.44% C, 4.-12% H, 15.60% N; Found: 62.31% C, 4.08% H, 15.39% N 3-(3-Fluorophenylsulfanyl)-1H-pyrrolo[3,2-b]pyridine-2-carboxylic acid amide, Ia-2

Treat 1H-pyrrolo[3,2-b]pyridine-2-carboxylic acid amide 6a-1 (1.20 g, 74.4 mmol) in DMF (100 mL) with bis-(3-fluorophenyl)disulfide (1.90 g, 1.0 equiv) as described in General Synthetic Procedure IVb to provide Ia-2 as an ivory colored solid (1.73 g, 80.8%), mp 235-237° C., tlc R$_f$=0.49.

¹H NMR (DMSO-d₆) δ 12.52 (bs, 1H), 8.45 (dd, 1H, J=1.2, 4.5 Hz), 8.10 (bs, 1H), 7.90 (dd, 1H, J=1.2, 8.2 Hz), 7.83 (bs, 1H), 7.27 (overlapping dd, 1H, J=4.5, 8.2 Hz and dd, J=7.8, 14.0 Hz, 1H), 6.97-6.82 (m, 3H); MS Obs 288 (M +1); LC/MS: a=100%. Analysis: Calcd. For $C_{14}H_{10}FN_3SO$: C, 58.53; H, 3.51; N, 14.62. Found: C, 57.95; H, 3.54; N, 14.25.

3-(3-Chlorophenylsulfanyl)-1H-pyrrolo[3,2-b]pyridine-2-carboxylic acid amide, Ia-3

Treat 1H-pyrrolo[3,2-b]pyridine-2-carboxylic acid amide 6a-1 (1.20 g, 74.4 mmol) in DMF (100 mL) with bis-(3-chlorophenyl)disulfide (2.13 g, 1.0 equiv) as described in General Synthetic Procedure IVb to provide Ia-3 as an ivory colored solid (1.95 g, 86.3%), mp 246.5-248° C., tlc $R_f$=0.49. ¹H NMR (DMSO-d₆) δ 12.54 (bs, 1H), 8.45 (dd; 1H, J=1.2, 4.5 Hz), 8.11 (bs, 1H), 7.90 (dd, 1H, J=1.3, 8.3 Hz) overlapping with 7.84 (bs, 1H), 7.31 (dd, 1H, J=4.5, 8.2 Hz) 7.22 (m, 2H), 7.06-6.99 (m, 2H). Analysis: Calcd. For $C_{14}H_{10}ClN_3SO$: C, 55.36; H, 3.32; N, 13.83. Found: C, 54.94; H, 3.26; N, 13.62.

3-(3-Bromophenylsulfanyl)-1H-pyrrolo[3,2-b]pyridine-2-carboxylic acid amide, Ia-4

Treat 1H-pyrrolo[3,2-b]pyridine-2-carboxylic acid amide 6a-1 (1.0 equiv) in DMF with bis-(3-bromophenyl)disulfide (1.1 equiv) as described in General Synthetic Procedure IVb to provide Ia-4 as an ivory colored solid. ¹H NMR (DMSO-d₆) δ 12.55 (bs, 1H), 8.46 (dd, 1H, J=1.2, 4.5 Hz), 8.10 (bs, 1H), 7.91 (dd, 1H, J=1.2, 8.2 Hz) overlapping with 7.85 (bs, 1H), 7.33 (dd, 1H, J=4.7, 8.5 Hz), 7.20 (m, 2H), 7.05-7.00 (m, 2H). MS Obs 348.1 (M+1).

3-(2-Chlorophenylsulfanyl)-1H-pyrrolo[3,2-b]pyridine-2-carboxylic acid amide, Ia-5

Treat 1H-pyrrolo[3,2-b]pyridine-2-carboxylic acid amide 6a-1 (1.0 equiv) in DMF with bis-(2-chlorophenyl)disulfide (1.1 equiv) as described in General Synthetic Procedure IVb to provide Ia-5 as an ivory colored solid. ¹H NMR (DMSO-d₆) δ 12.61 (bs, 1H), 8.46 (dd, 1H, J=1.0, 4.5 Hz), 8.09 (bs, 1H), 7.95 (d, 1H, J=8.0 Hz), 7.76 (bs, 1H), 7.49 (dd, 1H, J=1.5, 7.5 Hz), 7.34 (dd, 1H, J=4.5, 8.0 Hz), 7.14 (dt, 1H, J=1.5, 7.5 Hz), 7.08 (dt, 1H, J=1.5, 7.5 Hz), 6.49 (dd, 1H, J=1.5, 7.5 Hz). MS Obs 304.7 (M +1).

3-(4-Chlorophenylsulfanyl)-1H-pyrrolo[3,2-b]pyridine-2-carboxylic acid amide, Ia-6

Treat 1H-pyrrolo[3,2-b]pyridine-2-carboxylic acid amide 6a-1 (1.0 equiv) in DMF with bis-(4-chlorophenyl)disulfide (1.1 equiv) as described in General Synthetic Procedure IVb to provide Ia-6 as an ivory colored solid, mp=266° C., MS Obs 304.7 (M+1).

3-(2,4-Dichlorophenylsulfanyl)-1H-pyrrolo[3,2-b]pyridine-2-carboxylic acid amide, Ia-7

Treat 1H-pyrrolo[3,2-b]pyridine-2-carboxylic acid amide 6a-1 (1.0 equiv) in DMF with bis-(2,4-dichlorophenyl)disulfide (1.1 equiv) as described in General Synthetic Procedure IVb to provide Ia-7 as an ivory colored solid, mp=266° C., MS Obs 339.2 (M+1).

3-(2-Fluorophenylsulfanyl)-1H-pyrrolo[3,2-b]pyridine-2-carboxylic acid amide, Ia-8

Treat 1H-pyrrolo[3,2-b]pyridine-2-carboxylic acid amide 6a-1 (1.0 equiv) in DMF with bis-(2-fluorophenyl)disulfide (1.1 equiv) as described in General Synthetic Procedure IVb to provide Ia-8 as an ivory colored solid. ¹H NMR (DMSO-d₇) δ 12.57 (bs, 1H), 8.45 (dd, 1H, J=1.2, 4.2 Hz), 8.15 (bs, 1H), 7.90 (dd, 1H, J=1.2, 8.1 Hz) overlapping with 7.84 (bs, 1H), 7.31 (dd, 1H, J=4.5, 8.2 Hz), 7.20 (m, 2H), 6.98 (m, 1H), 6.69 (m, 1H). MS Obs 288.2 (M+1).

3-(2,3-Dichlorophenylsulfanyl)-1H-pyrrolo[3,2-b]pyridine-2-carboxylic acid amide, Ia-9

Treat 1H-pyrrolo[3,2-b]pyridine-2-carboxylic acid amide 6a-1 (1.0 equiv) in DMF with bis-(2,3-dichlorophenyl)disulfide (1.1 equiv) as described in General Synthetic Procedure IVb to provide Ia-9 as an ivory colored solid. ¹H NMR (DMSO-d₆) δ 12.62 (bs, 1H), 8.44 (dd, 1H, J=1.2, 4.5 Hz), 8.10 (bs, 1H), 7.93 (dd, 1H, J=1.2, 8.3 Hz), 7.75 (bs, 1H), 7.35 (m, 2H), 7.07 (t, 1H, J=8.1 Hz), 6.40 (dd, 1H, J=1.4, 8.1 Hz). MS Obs 338.1 (M+1).

3-(2-Trifluormethylphenylsulfanyl)-1H-pyrrolo[3,2-b]pyridine-2-carboxylic acid amide, Ia-10

Treat 1H-pyrrolo[3,2-b]pyridine-2-carboxylic acid amide 6a-1 (1.0 equiv) in DMF with bis-(2-trifluoromethylphenyl) disulfide (1.1 equiv) as described in General Synthetic Procedure IVb to provide Ia-10 as an ivory colored solid. ¹H NMR (DMSO-d₆) δ 12.65 (bs, 1H), 8.47 (dd, 1H, J=1.5, 4.5 Hz), 8.15 (bs, 1H), 7.92 (dd, 1H, J=1.2, 8.2 Hz), 7.75 (bs, overlapping dd, 2H), 7.34 (m, 3H), 6.75 (d, 1H, J=7.8 Hz); MS Obs 338.2 (M+1).

3-(3-Trifluoromethyl-phenylsulfanyl)-1H-pyrrolo[3,2-b]pyridine-2-carboxylic acid, amide Ia-11

Treat 1H-pyrrolo[3,2-b]pyridine-2-carboxylic acid amide 6a-1 (1.0 equiv) in DMF with bis-(3-trifluoromethylphenyl) disulfide (1.1 equiv) as described in General Synthetic Procedure IVb to provide Ia-11 as an ivory colored solid. MS Obs 338.06 (M+1).

3-(2-Aminophenylsulfanyl)-1H-pyrrolo[3,2-b]pyridine-2-carboxylic acid amide, Ia-12

Treat 1H-pyrrolo[3,2-b]pyridine-2-carboxylic acid amide (1.0 equiv) 6a-1 in DMF with bis-(2-aminophenyl)disulfide (1.1 equiv) as described in General Synthetic Procedure IVb to provide Ia-12 as an ivory colored solid. ¹H NMR (DMSO-d₆) δ 12.29 (bs, 1H), 8.49 (dd, 1H, J=1.3, 4.5 Hz), 8.18 and 8.15 (overlapping bs, 2H), 7.83 (dd, 1H, J=1.4, 8.2 Hz), 7.28 (dd, 1H, J=4.5, 8.3 Hz), 7.15 (dd, 1H, J=1.4, 7.8 Hz), 6.93 (m, 1H), 6.62 (d, 1H, J=6.9 Hz), 6.39 (m, 1H), 5.74 (overlapping bs, 2H); MS Obs 288.2 (M+1).

3-(2,5-Dichloro-phenylsulfanyl)-1H-pyrrolo[3,2-b]pyridine-2-carboxylic acid amide, Ia-13

Treat 1H-pyrrolo[3,2-b]pyridine-2-carboxylic acid amide 6a-1 (1.0 equiv) in DMF with bis-(2,5-dichlorophenyl)disulfide (1.1 equiv) as described in General Synthetic Procedure IVb to provide Ia-13 as an ivory colored solid. ¹H NMR (DMSO-d₆) δ 12.68 (bs, 1H), 8.46 (dd, 1H, J=1.3, 4.5 Hz), 8.10 (bs, 1H), 7.94 (dd, 1H, J=1.2, 8.2 Hz), 7.77 (bs, 1H), 7.52 (apparent d, 1H, J=8.5 Hz), 7.35 (dd, 1H, J=4.5, 8.4 Hz), 7.20 (dd, 1H, J=2.5, 8.5 Hz), 6.37 (apparent d, 1H, J=2.5 Hz); MS Obs 338.1 (M+1).

3-(2-Methoxy-phenylsulfanyl)-1H-pyrrolo[3,2-b]pyridine-2-carboxylic acid amide, Ia-14

Treat 1H-pyrrolo[3,2-b]pyridine-2-carboxylic acid amide 6a-1 (1.0 equiv) in DMF with bis-(2-methoxyphenyl)disulfide (1.1 equiv) as described in General Synthetic Procedure IVb to provide Ia-14 as an ivory colored solid. ¹H NMR (DMSO-d₆) δ 12.48 (bs, 1H), 8.44 (dd, 1H, J=1.5, 4.5 Hz), 8.10 (bs, 1H), 7.90 (dd, 1H, J=1.2, 8.0 Hz), 7.60 (bs, 1H), 7.30 (m, 3H), 6.71 (apparent t, 1H), 6.50 (apparent d, 1H), 3.91 (s, 3H); MS Obs 300.3 (M+1).

3-(3-Methoxy-phenylsulfanyl)-1H-pyrrolo[3,2-b]pyridine-2-carboxylic acid amide, Ia-15

Treat 1H-pyrrolo[3,2-b]pyridine-2-carboxylic acid amide 6a-1 (1.0 equiv) in DMF with bis-(3-methoxyphenyl)disulfide (1.1 equiv) as described in General Synthetic Procedure IVb to provide Ia-15 as an ivory colored solid. $^1$H NMR (DMSO-$d_6$) δ 12.51 (bs, 1H), 8.46 (dd, 1H, J=1.5, 4.5 Hz), 8.10 (bs, 1H), 7.89 (dd, 1H, J=1.5, 8.3 Hz overlapping with bs, 1H), 7.32 (dd, 1H, J=4.5, 8.2 Hz), 7.13 (apparent t, 1H, J=8.0 Hz) 6.62 (m, 3H), 3.64 (s, 3H); MS Obs 300.3 (M+1).

3-(3-Amino-phenylsulfanyl)-1H-pyrrolo[3,2-b]pyridine-2-carboxylic acid amide, Ia-16

Treat 1H-pyrrolo[3,2-b]pyridine-2-carboxylic acid amide 6a-1 (1.0 equiv) in DMF with bis-(3-aminophenyl)disulfide (1.1 equiv) as described in General Synthetic Procedure IVb to provide Ia-16 as an ivory colored solid. $^1$H NMR (DMSO-d,) δ 12.40 (bs, 1H), 8.44 (dd, 1H, J=1.5, 4.5 Hz), 8.10 (bs, 1H), 7.86 (dd, 1H, J=1.5, 8.3 Hz overlapping with bs, 1H), 7.28 (dd, 1H, J=4.5, 8.2 Hz), 7.13 (apparent t, 1H, J=7.8 Hz) 6.28 (m, 3H), 5.08 (bs, 2H); MS Obs 288.08 (M+1).

3-(4-Nitro-phenylsulfanyl)-1H-pyrrolo[3,2-b]pyridine-2-carboxylic acid amide, Ia-17

Treat 1H-pyrrolo[3,2-b]pyridine-2-carboxylic acid amide 6a-1 (1.0 equiv) in DMF with bis-(4-nitrophenyl)disulfide (1.1 equiv) as described in General Synthetic Procedure IVb to provide Ia-17 as an ivory colored solid. $^1$H NMR (DMSO-$d_6$) δ 12.63 (bs, 1H), 8.43 (dd, 1H, J=1.5, 4.5 Hz), 8.05 (m, 3H), 7.91 (m, 1H), 7.50 (bs, 1H), 7.32 (dd, 1H, J=4.5, 8.1 Hz), 7.18 (apparent d, 2H, J=9.0 Hz); MS Obs 315.05 (M+1).

3-(3-Nitro-phenylsulfanyl)-1H-pyrrolo[3,2-b]pyridine-2-carboxylic acid amide, Ia-18

Treat 1H-pyrrolo[3,2-b]pyridine-2-carboxylic acid amide 6a-1 (1.0 equiv) in DMF with bis-(3-nitrophenyl)disulfide (1.1 equiv) as described in General Synthetic Procedure IVb to provide Ia-18 as an ivory colored solid. $^1$H NMR (DMSO-$d_6$) δ 12.59 (bs, 1H), 8.45 (dd, 1H, J=1.5, 4.6 Hz), 8.11 (bs, 1H), 7.96-7.81 (m, 4H), 7.50 (m, 2H), 7.33 (dd, 1H, J=4.5, 8.4 Hz); Obs 315.1 (M+1).

3-o-Tolylsulfanyl-1H-pyrrolo[3,2-b]pyridine-2-carboxylic acid amide, Ia-19.

Treat 1H-pyrrolo[3,2-b]pyridine-2-carboxylic acid amide 6a-1 (1.0 equiv) in DMF with bis-(o-tolyl)disulfide (1.1 equiv) as described in General Synthetic Procedure IVb to provide Ia-19 as an ivory colored solid. $^1$H NMR (DMSO-$d_6$) δ 12.5 (bs, 1H), 8.41 (dd, 1H, J=1.5, 4.5 Hz), 8.05 (bs, 1H), 7.90 (dd, 1H, J=1.5, 8.3 Hz) overlapping with 7.87 (bs, 1H), 7.31 (m, 1H), 7.29 (m, 1H), 7.00 (m, 2H), 6.4 (m, 1H), 3.3 (s, 3H). MS Obs 284.3 (M+1).

3-p-Tolylsulfanyl-1H-pyrrolo[3,2-b]pyridine-2-carboxylic acid amide, Ia-20

Treat 1H-pyrrolo[3,2-b]pyridine-2-carboxylic acid amide 6a-1 (1.0 equiv) in DMF with bis-(p-tolyl)disulfide (1.1 equiv) as described in General Synthetic Procedure IVb to provide Ia-20 as an ivory colored solid. $^1$H NMR (DMSO-$d_6$) δ 12.42 (bs, 1H), 8.44 (dd, 1H, J=1.5, 4.5 Hz), 8.10 (bs, 1H), 7.91 (bs, 1H) overlapping with 7.86 (dd, 1H, J=1.5, 7.9 Hz), 7.28 (dd, 1H, J=3.7, 8.3 Hz), 7.00 (overlapping ds, 4H, J=12.5 Hz), 3.31 (s, 3H); MS Obs 284 (M+1).

3-(3,5-Dimethyl-phenylsulfanyl)-1H-pyrrolo[3,2-b]pyridine-2-carboxylic acid amide, Ia-21

Treat 1H-pyrrolo[3,2-b]pyridine-2-carboxylic acid amide 6a-1 (1.0 equiv) in DMF with bis-(3,5-dimethylphenyl)disulfide (1.1 equiv) as described in General Synthetic Procedure IVb to provide Ia-21 as an ivory colored solid. $^1$H NMR (DMSO-$d_6$) δ 12.45 (bs, 1H), 8.45 (dd, 1H, J=1.2, 4.5 Hz), 8.12 (bs, 1H), 7.90 (dd, 1H, J=1.2, 8.0 Hz) overlapping with (bs, 1H), 7.3 (dd, 1H, J=4.5, 8.2 Hz), 6.76 (s, 1H), 6.7 (s, 2H), 2.05 (s, 6H). MS Obs 298.3 (M+1).

3-m-Tolylsulfanyl-1H-pyrrolo[3,2-b]pyridine-2-carboxylic acid amide, Ia-22

Treat 1H-pyrrolo[3,2-b]pyridine-2-carboxylic acid amide 6a-1 (1.0 equiv) in DMF with bis-(m-tolyl)disulfide (1.1 equiv) as described in General Synthetic Procedure IVb to provide Ia-22 as an ivory colored solid. $^1$H NMR (DMSO-$d_6$) δ 10.2 (bs, 1H), 8.62 (dd, 1H, J=1.0, 4.4 Hz), 8.19 (bs, 1H), 7.85 (dd, 1H, J=1.3, 8.4 Hz), 7.28 (overlapping dd, 1H, J=4.5, 8.3 Hz and 7.24 (s, 1H), 7.1-6.9 (m, 4H), 2.22 (s, 3H). MS Obs 284 (M+1).

3-(2-Ethyl-phenylsulfanyl)-1H-pyrrolo[3,2-b]pyridine-2-carboxylic acid amide, Ia-23

Treat 1H-pyrrolo[3,2-b]pyridine-2-carboxylic acid amide 6a-1 (1.0 equiv) in DMF with bis-(2-ethylphenyl)disulfide (1.1 equiv) as described in General Synthetic Procedure IVb to provide Ia-23 as an ivory colored solid. $^1$H NMR (DMSO-$d_6$) δ 12.5 (bs, 1H), 8.42 (dd, 1H, J=1.5, 4.4 Hz), 8.1 (bs, 1H), 7.91 (dd, 1H, J=1.5, 8.1 Hz), 7.82 (bs, 1H), 7.30 (m, 1H), 7.2 (m, 1H), 7.05 (m, 1H), 6.95 (m, 1H), 6.5 (m, 1H), 2.9 (q, 2H), 1.3 (t, 3H). MS Obs 298.3 (M+1).

3-(3-Trifluoromethoxy-phenylsulfanyl)-1H-pyrrolo[3,2-b]pyridine-2-carboxylic acid, amide, Ia-24

Treat 1H-pyrrolo[3,2-b]pyridine-2-carboxylic acid amide 6a-1 (1.0 equiv) in DMF with bis-(3-trifluoromethoxyphenyl)disulfide (1.1 equiv) as described in General Synthetic Procedure IVb to provide Ia-24 as an ivory colored solid. $^1$H NMR (DMSO-$d_6$) δ 12.56 (bs, 1H), 8.45 (dd, 1H, J=1.5, 4.5 Hz), 8.12 (bs, 1H), 7.92 (dd, 1H, J=1.5, 8.3 Hz), 7.85 (bs, 1H), 7.33 (dd, 1H, J=4.4, 8.3 Hz) overlapping with 7.32 (m, 1H), 7.1 (m, 1H) overlapping with 7.03 (m, 2H). MS Obs 354.1 (M+1).

3-(Quinolin-8-ylsulfanyl)-1H-pyrrolo[3,2-b]pyridine-2-carboxylic acid amide, Ia-25

Treat 1H-pyrrolo[3,2-b]pyridine-2-carboxylic acid amide 6a-1 (1.0 equiv) in DMF with bis-(8-quinolyl)disulfide (1.1 equiv) as described in General Synthetic Procedure IVb to provide Ia-25 as an ivory colored solid, MS Obs 321.1 (M+1).

3-(Pyridin-2-sulfanyl)-1H-pyrrolo[3,2-b]pyridine-2-carboxylic acid amide, Ia-26

Treat 1H-pyrrolo[3,2-b]pyridine-2-carboxylic acid amide 6a-1 (1.0 equiv) in DMF with 2,2'-dipyridyl disulfide (1.1 equiv) as described in General Synthetic Procedure IVb to provide Ia-26 as an ivory colored solid. $^1$H NMR (DMSO-$d_6$) δ 12.51 (bs, 1H), 8.42 (dd, 1H, J=1.4, 4.5 Hz), 8.34 (dd, 1H, J=1, 4 Hz) 8.06 (bs, 1H), 7.89 (dd, 1H, J=1.4, 8.3 Hz) overlapping with 7.82 (bs, 1H), 7.53 (dd, 1H, J=1.8, 7.5 Hz), 7.30 (dd, 1H, J=4.3, 8.2 Hz), 7.10 (dd, 1H, J=4.9, 7.4 Hz), 6.74 (d, 1H, J=8.1 Hz). MS Obs 271.1 (M+1).

3-(Pyridin-4-sulfanyl)-1H-pyrrolo[3,2-b]pyridine-2-carboxylic acid amide, Ia-27

Treat 1H-pyrrolo[3,2-b]pyridine-2-carboxylic acid amide 6a-1 (1.0 equiv) in DMF with 4,4'-dipyridyl disulfide (Aldrithiol 4) (1.1 equiv) as described in General Synthetic Procedure IVb to provide Ia-27 as an ivory colored solid. $^1$H NMR (DMSO-$d_6$) δ 12.5 (bs, 1H), 8.44 (dd, 1H, J=1.5, 4.5 Hz), 8.27 (dd, 2H, J=1.5, 4.5 Hz), 8.07 (bs, 1H), 7.93 (dd, 1H, J=1.4, 8.3 Hz), 7.73 (bs, 1H), 7.33 (dd, 1H, J=4.5, 8.2 Hz), 6.94 (dd, 2H, J=1.5, 4.5 Hz). MS Obs 271.07 (M+1).

3-(Thiophen-2-ylsulfanyl)-1H-pyrrolo[3,2-b]pyridine-2-carboxylic acid amide, Ia-28

Treat 1H-pyrrolo[3,2-b]pyridine-2-carboxylic acid amide 6a-1 (1.0 equiv) in DMF with 2,2'bis(thienyl)disulfide (1.1 equiv) as described in General Synthetic Procedure IVb to provide Ia-28 as an ivory colored solid. $^1$H NMR (DMSO-$d_6$)

δ 12.34 (bs, 1H), 8.50 (d, 1H, J=4.4 Hz), 8.21 (bs, 1H), 8.00 (bs, 1H), 7.83 (d, 1H, J=8.3 Hz), 7.42 (d, 1H, J=5.3 Hz), 7.26 (dd, 2H, J=4.5, 8.2 Hz), 6.92 (dd, 1H, J=3.6, 5.2 Hz). MS Obs 276.01 (M+1).

1-Methyl-3-phenylsulfanyl-1H-pyrrolo[3,2-b]pyridine-2-carboxylic acid methylamide, Ia-29

Treat 3-phenylsulfanyl-1H-pyrrolo[3,2-b]pyridine-2-carboxylic acid methylamide Ia-33 (1.0 equiv) in DMF with dimethylsulfate (1.5 equiv) as described in General Synthetic Procedure V to provide Ia-29 as an ivory colored solid, MS Obs 298.09 (M+1).

1-Methyl-3-phenylsulfanyl-1H-pyrrolo[3,2-b]pyridine-2-carboxylic acid methylamide, Ia-29

Add methyl iodide (20 mg, 0.164 mmol) at r.t. to a mixture of 3-phenylsulfanyl-1H-pyrrolo[3,2-b]pyridine-2-carboxylic acid methylamide (Ia-33, 47 mg, 0.166 mmol), $Cs_2CO_3$ (65 mg, 0.2 mmol) and pyridine (1.5 mL). Heat the reaction at 60° C. in a sealed vessel for 3 hrs. Add additional methyl iodide (20 mg) and moniter the progress on the reaction by chromatography. When complete, cool the mixture, concentrate to dryness and extract into ethyl acetate from brine. Separate the organic phase and concentrate. Purify the residue by flash chromatography twice ($SiO_2$, 3 gm, elute with MeOH 0-4% in DCM; and $SiO_2$, 1 gm, elute with heptane:DCM, 1:1) to provide title compound (10 mg) as a white solid, $^1$H NMR ($CDCl_3$) and LC-MS (m/e=297) were consistent for the title compound structure.

3-(3-Trifluoromethyoxyphenylsulfanyl-1H-pyrrolo[3,2-b]pyridine-2-carboxylic acid methylamide, Ia-30.

Treat 1H-pyrrolo[3,2-b]pyridine-2-carboxylic acid methylamide 6a-2 (1.0 equiv) in DMF with bis-(3-trifluormethoxyphenyl)disulfide (1.1 equiv) as described in General Synthetic Procedure IVb to provide Ia-30 as an ivory colored solid, MS Obs 368.03 (M+1).

3-(3-Chlorophenylsulfanyl-1H-pyrrolo[3,2-b]pyridine-2-carboxylic acid methylamide, Ia-31

Treat 1H-pyrrolo[3,2-b]pyridine-2-carboxylic acid methylamide 6a-2 (1.0 equiv) in DMF with bis-(3-chlorophenyl)disulfide (1.1 equiv) as described in General Synthetic Procedure IVb to provide Ia-31 as an ivory colored solid, MS Obs 318.03 (M+1).

3-(3-Fluorophenylsulfanyl-1H-pyrrolo[3,2-b]pyridine-2-carboxylic acid methylamide, Ia-32

Treat 1H-pyrrolo[3,2-b]pyridine-2-carboxylic acid methylamide 6a-2 (1.0 equiv) in DMF with bis-(3-fluorophenyl)disulfide (1.1 equiv) as described in General Synthetic Procedure IVb to provide Ia-32 as an ivory colored solid, MS Obs 305.05 (M+1).

3-Phenylsulfanyl-1H-pyrrolo[3,2-b]pyridine-2-carboxylic acid methylamide, Ia-33

Treat 1H-pyrrolo[3,2-b]pyridine-2-carboxylic acid methylamide 6a-2 (1.0 equiv) in DMF with bis-(phenyl)disulfide (1.1 equiv) as described in General Synthetic Procedure IVb to provide Ia-33 as an ivory colored solid. $^1$H NMR (DMSO-$d_6$) δ 12.48 (bs, 1H), 8.45 (dd, 1H, J=1.5, 4.4 Hz), 8.11 (bs, 1H), 7.89 (dd, 1H, J=1.5, 4.0 Hz overlapping with a bs, 1H), 7.31 (dd, 1H, J=1.4, 4.5 Hz), 7.28 (dd, J=1.5, 4.5 Hz, 1H) 7.21 (m, 2H), 7.13-7.05 (m, 3H), 2.9 (d, 3H, J=4.2 Hz); MS Obs 284.06 (M+1).

1-Methyl-3-phenylsulfanyl-1H-pyrrolo[3,2-b]pyridine-2-carboxylic acid amide, Ia-34

Treat 3-phenylsulfanyl-1H-pyrrolo[3,2-b]pyridine-2-carboxylic acid amide Ia-1 (1.0 equiv) in DMF with dimethylsulfate (1.5 equiv) as described in General Synthetic Procedure V to provide Ia-34 as an ivory colored solid, MS Obs 284.06 (M+1).

1-Methyl-3-phenylsulfanyl-1H-pyrrolo[3,2-b]pyridine-2-carboxylic acid amide, Ia-34 (Scheme I, step g)

Add methyl iodide (20 mg, 0.14 mmol) at r.t. to a mixture of 3-phenylsulfanyl-1H-pyrrolo[3,2-b]pyridine-2-carboxylic acid amide (Ia-1, 27 mg, 0.1 mmol), $Cs_2CO_3$ (43 mg, 0.13 mmol) in pyridine (0.5 ml). Heat the reaction at 80° C. in a sealed vessel for 15 minutes. Cool the mixture cooled and extract into ethyl acetate from water. Separate the organic solution and evaporate. Purify the residue (33 mg) by flash chromatography (silica gel, 3 gm, elute with MeOH 0-4% in dichloromethane) to provide the title compound (11 mg) as a white solid, $^1$H NMR ($CDCl_3$) and LC-MS (m/e=283) are consistent for the title compound structure.

3-(3-Fluoro-phenylsulfanyl)-5-methoxy-1H-pyrrolo[3,2-b]pyridine-2-carboxylic acid amide, Ia-35

Treat 5-methoxy-1H-pyrrolo[3,2-b]pyridine-2-carboxylic acid amide (1.0 equiv, prepared from the corresponding ethyl ester, Frydman, B.; Reil, S. J.; Boned, J.; Rapoport, H. J. Org. Chem. 1968, 33, 3762-6) in DMF with bis-(3-fluorophenyl)disulfide (1.1 equiv) as described in General Synthetic Procedure IVb to provide Ia-35 as an ivory colored solid, MS Obs 318.03 (M+1).

3-(3-Methoxy-phenylsulfanyl)-5-methoxy-1H-pyrrolo[3,2-b]pyridine-2-carboxylic acid amide, Ia-36

Treat 5-methoxy-1H-pyrrolo[3,2-b]pyridine-2-carboxylic acid amide (1.0 equiv, prepared from the corresponding ethyl ester, Frydman, B.; Reil, S. J.; Boned, J.; Rapoport, H. J. Org. Chem. 1968, 33, 3762-6) in DMF with bis-(3-methoxyphenyl)disulfide (1.1 equiv) as described in General Synthetic Procedure IVb to provide Ia-36 as an ivory colored solid, MS Obs 330.01 (M+1).

3-Phenylsulfanyl-1-propyl-1H-pyrrolo[3,2-b]pyridine-2-carboxylic acid amide, Ia-37

Treat 3-phenylsulfanyl-1H-pyrrolo[3,2-b]pyridine-2-carboxylic acid amide Ia-1 (1.0 equiv) in DMF with propyliodide (1.5 equiv) in the presence of $Cs_2CO_3$ (1.5 equiv.) according to General Procedure V to provide Ia-37 as an ivory colored solid after chromatography, MS Obs 312.06 (M+1).

3-Phenylsulfanyl-1-propyl-1H-pyrrolo[3,2-b]pyridine-2-carboxylic acid amide, Ia-37 (Scheme I, step g)

Add 1-bromopropane (19 mg, 0.154 mmol) at r.t. to a mixture of 3-phenylsulfanyl-1H-pyrrolo[3,2-b]pyridine-2-carboxylic acid amide (Ia-1, 31.5 mg, 0.12 mmol), $Cs_2CO_3$ (60 mg, 0.185 mmol) in pyridine (0.5 ml). Heat the reaction at 80° C. in a sealed vessel for 1 hr. Cool the mixture and extract into ethyl acetate from water. Separate the organic phase and evaporate. Purify the residue (33 mg) by flash chromatography ($SiO_2$, 2 gm, elute with heptane:DCM then MeOH 0-4% in DCM) to provide title compound (11.5 mg) as a white solid, $^1$H NMR ($CDCl_3$) and LC-MS (m/e=311) are consistent for the title compound structure.

Preparation of Pyrrolo[3,2-c]indoles (5-Azaindoles)

2-(Diethoxymethyl)-1H-pyrrolo[3,2-c]pyridine-1-carboxylic acid 1,1-dimethylethyl ester, 8b-1 (Scheme 3, step h)

Heat a solution of (3-iodo-pyridin-4-yl)carbamic acid 1,1-dimethylethyl ester (13.3 g, 41.56 mmol, Darnbrough, Shelley; Mervic, Miljenko; Condon, Stephen M.; Burns, Christopher J. Synthetic Communications (2001) 31(21), 3273-3280), 3,3-diethoxy-1-propyne (5.96 ml, 41.56 mmole), triethylamine (23 ml, 166 mmol), dichlorobis(triphenylphospine)palladium(II) (1.46 g, 2.08 mmol) and copper iodide (237 mg, 1.25 mmol) in dry DMF under argon to 90° C. for 3 h. Allow the reaction mixture to cool to 70° C. and add DBU (12.5 ml, 83.12 mmol). Stir the reaction at 70° C. for 3 h and then stir at room temperature overnight. Pour the reaction mixture into EtOAc, wash with water (2×) and brine, dry over $MgSO_4$, filter and concentrate to give the title compound as an oil. Purify the oil by flash chromatography (silica, elute with 10-20% EtOAc/n-heptane) to provide 9.8 g of the title compound as a clear oil, tlc (silica, 30% EtOAc/heptane, $R_f$=0.30).

1H-Pyrrolo[3,2-c]pyridine-2-carboxaldehyde, 9b-1 (Scheme 3, step i)

Add to a solution of 2-(diethoxymethyl)-1H-pyrrolo[3,2-c]pyridine-1-carboxylic acid 1,1-dimethylethyl ester (8b-1, 9.8 g, 30.6 mmol) in 100 ml THF, 6 ml of concentrated HCl. Stir the reaction mixture at room temperature for 20 h, basify with saturated sodium bicarbonate solution, pour into EtOAc, wash with saturated sodium bicarbonate and brine, dry the organic phase over $MgSO_4$, filter, and concentrate to give a mixture of 2-formyl-1H-pyrrolo[3,2-c]pyridine-1-carboxylic acid 1,1-dimethylethyl ester and 1H-pyrrolo[3,2-c]pyridine-2-carboxaldehyde 9b-1 as a solid. Separate the mixture by flash chromatography (silica, 1-3% $MeOH/CH_2Cl_2$) to give 2-formyl-1H-pyrrolo[3,2-c]pyridine-1-carboxylic acid 1,1-dimethylethyl ester (5.0 g) as an oil and 1H-pyrrolo[3,2-c]pyridine-2-carboxaldehyde 9b-1 (1.0 g) as a tan solid. Add TFA (5.0 mL) dropwise to a solution of 2-formyl-1H-pyrrolo[3,2-c]pyridine-1-carboxylic acid 1,1-dimethylethyl ester (5.0 g, 20.3 mmol) in 250 ml dichloromethane. Heat the reaction mixture at reflux for 3 hours, concentrate, dilute the residue with 300 ml EtOAc, wash with saturated sodium bicarbonate solution (3×) and brine, dry the organic phase ($MgSO_4$), filter and concentrate to yield 1H-pyrrolo[3,2-c]pyridine-2-carboxaldehyde 9b-1 (2.24 g) as a pure solid.

1H-Pyrrolo[3,2-c]pyridine-2-carboxylic acid methyl ester, 5b-1 (Scheme 3, step j)

Add to a 0° C. solution of 1H-pyrrolo[3,2-c]pyridine-2-carboxaldehyde (9b-1, 3.24 g, 22.19 mmol) in methanol under argon, sodium cyanide (5.44 g, 111 mmol) and manganese dioxide (9.65 g, 111 mmol). Stir the reaction mixture for 5 h, filter through Celite® and dilute with 500 ml EtOAc. Wash the organic layer with water (2×) and brine, dry over sodium carbonate, filter, and concentrate to provide the title compound (3.27 g) as a pure tan solid. Prepare 1H-pyrrolo[3,2-c]pyridine-2-carboxylic acid amide 6b-1 from 5b-1 by any of the above described procedures for the synthesis compound 6a-1 from ethyl ester 4a-1.

1H-Pyrrolo[3,2-c]pyridine-2-carboxylic acid amide, 6b-1 ($R_4$=H, Scheme 1, steps a-c, e)

Prepare 3-methyl-4-nitro-pyridine (2b-1) from 3-chloro-4-nitro-pyridine 1b-1 as described above for the synthesis of the isomeric 2-methyl-3-nitro-pyridine analog 2a-1 from compound 1a-1. Prepare 2-hydroxy-3-(4-nitro-pyridin-3-yl)-acrylic acid ester (3b-1) from compound 2b-1 by any of the above described procedures for the preparation of compound 3a-1 from compound 2a-1. Prepare 1H-pyrrolo[3,2-c]pyridine-2-carboxylic acid ethyl ester, 4b-1, from compound 3b-1 by any of the above described procedures for the preparation of compound 4a-1 from compound 3a-1. Prepare 1H-pyrrolo[3,2-c]pyridine-2-carboxylic acid amide 6b-1 from compound 4b-1 by any of the above described procedures for the synthesis compound 6a-1 from compound 4a-1.

3-Phenylsulfanyl-1H-pyrrolo[3,2-c]pyridine-2-carboxylic acid amide, Ib-1

Treat 1H-pyrrolo[3,2-c]pyridine-2-carboxylic acid amide 6b-1 (1.0 equiv) in DMF (100 mL) with diphenyldisulfide (1.1 equiv) as described above in General Procedure IVb to provide I-1 as an ivory colored solid: $^1$H NM (DMSO-$d_6$) δ 12.48 (bs, 1H), 8.70 (s, 1H), 8.29 (d, J=5.8 Hz, 1H), 8.04 (bs, 1H), 7.76 (bs, 1H), 7.44 (dd, J=1.1, 5.7 Hz, 1H), 7.26 (m, 2H), 7.14 (m, 3H); m/z=270.1 (M+H).

3-(3-Fluoro-phenylsulfanyl-1H-pyrrolo[3,2-c]pyridine-2-carboxylic acid amide, Ib-2

Treat 1H-pyrrolo[3,2-c]pyridine-2-carboxylic acid amide 6b-1 (1.0 equiv) in DMF (100 mL) with bis-(3-fluorophenyl)disulfide (1.1 equiv) as described above in General Procedure IVb to provide Ib-2 as an ivory colored solid: $^1$H NMR (DMSO-$d_6$) δ 12.63 (bs, 1H), 8.71 (s, 1H), 8.31 (d, J=5.8 Hz, 1H), 8.06 (bs, 1H), 7.74 (bs, 1H), 7.46 (d, J=5.8 Hz, 1H), 7.3 (m, 1H), 6.99-6.89 (overlapping m, 3H); m/z=288.06 (M+1).

3-(4-Chloro-phenylsulfanyl-1H-pyrrolo[3,2-c]pyridine-2-carboxylic acid amide, Ib-3

Treat 1H-pyrrolo[3,2-c]pyridine-2-carboxylic acid amide 6b-1 (1.0 equiv) in DMF (100 mL) with bis-(4-chlorophenyl)disulfide (1.1 equiv) as described above in General Procedure IVb to provide Ib-3 as an ivory colored solid: $^1$H NMR (DMSO-$d_6$) δ 12.61 (bs, 1H), 8.71 (bs, 1H), 8.30 (d, 1H, J=4.5 Hz), 8.07 (bs, 1H), 7.76 (bs, 1H), 7.45 (d, 1H, J=5.7 Hz), 7.32 (d, 2H, J=8.7 Hz), 7.12 (d, 2H, J=8.5 Hz), m/z=304 (M+1).

Preparation of Pyrrolo[2,3-c]indoles (6-Azaindoles)

1H-Pyrrolo[2,3-c]pyridine-2-carboxylic acid amide, 6c-i ($R_4$=H, Scheme 1, steps a-c, e)

Prepare 4-methyl-3-nitro-pyridine (2c-1) from 4-chloro-3-nitro-pyridine 1c-1 as described above for the synthesis of the isomeric 2-methyl-3-nitro-pyridine analog 2a-1 from compound 1a-1. Prepare 2-hydroxy-3-(3-nitro-pyridin-4-yl)-acrylic acid ester (3c-1) from compound 2c-1 by any of the above described procedures for the preparation of compound 3a-1 from compound 2a-1. Prepare 1H-pyrrolo[2,3-c]pyridine-2-carboxylic acid ethyl ester (4c-1) from compound 3c-1 by any of the above described procedures for the preparation of compound 4a-1 from compound 3a-1. Prepare 1H-pyrrolo[2,3-c]pyridine-2-carboxylic acid amide 6c-1 from compound 4c-1 by any of the above described procedures the synthesis compound 6a-1 from compound 4a-1.

3-Phenylsulfanyl-1H-pyrrolo[2,3-c]pyridine-2-carboxylic acid amide, Ic-1

Add to 1H-pyrrolo[2,3-c]pyridine-2-carboxylic acid amide 6c-1 (1.0 equiv) in DMF (100 mL), (diphenyl)disulfide (1.0 equiv) as described above in General Procedure IVb to provide Ic-1 as a tan crystalline solid: $^1$H NMR (DMSO-$d_6$) δ 12.4 (bs, 1H), 8.86 (s, 1H), 8.18 (m, 2H), 7.84 (bs, 1H), 7.42 (d, J=5.5 Hz, 1H), 7.24 (m, 2H), 7.14 (m, 1H), 7.03 (d, 8.3 Hz, 2H); m/z=270.1 (M+H).

3-Benzenesulfonyl-1H-pyrrolo[2,3-c]pyridine-2-carboxylic acid amide, Ic-2

Treat 3-phenylsulfanyl-1H-pyrrolo[2,3-c]pyridine-2-carboxylic acid amide 6c-1 (1.0 mmol) with $H_2O_2$ (30% w/v, 131 μL, 2.5 mmol) and $Na_2CO_3$ (212 mg, 2.0 mmol). Stir at rt for 16 h, quench the reaction with $H_2O$, and extract with EtOAc. Wash the extract with brine, dry the organic phase ($MgSO_4$) and concentrate to give Ic-2 as an ivory colored solid; MS Obs 303 (M+1).

3-(3-Fluoro-phenylsulfanyl)-1H-pyrrolo[2,3-c]pyridine-2-carboxylic acid amide, Ic-3

Treat 1H-pyrrolo[2,3-c]pyridine-2-carboxylic acid amide 6c-1 (1.0 equiv) in DMF (100 mL) with bis-(3-fluorophenyl)disulfide (1.0 equiv) as described above in General Procedure IVb to give Ic-3 as a tan solid: $^1$H NMR (DMSO-d$_6$) δ 12.77 (bs, 1H), 8.87 (s, 1H), 8.2 (d, J=5.2 Hz, 1H) partially overlapping with 8.13 (bs, 1H), 7.81 (bs, 1H), 7.42 (d, J=5.5 Hz, 1H), 7.26 (m, 1H), 6.96 (m, 1H), 6.84 (m, 2H); m/z=288.04 (M+H).

3-(3-Methoxy-phenylsulfanyl)-1H-pyrrolo[2,3-c]pyridine-2-carboxylic acid amide, Ic-4

Treat 1H-pyrrolo[2,3-c]pyridine-2-carboxylic acid amide 6c-1 (1.0 equiv) in DMF (100 mL) with bis-(3-methoxyphenyl)disulfide (1.0 equiv) as described above in General Procedure IVb to give Ic-4 as a tan solid: $^1$H NMR (DMSO-d$_6$) δ 12.8 (bs, 1H), 8.89 (s, 1H), 8.2 (d, J=5.3 Hz, 1H) overlapping with 8.19 (bs, 1H), 7.81 (bs, 1H), 7.41 (d, J=5.4 Hz, 1H), 7.19 (m, 1H), 6.61 (s, 1H), partially overlapped with 6.56 (m, 2H), 3.65 (s, 3H); m/z=300.1 (M+H).

3-(3-Chloro-phenylsulfanyl)-1H-pyrrolo[2,3-c]pyridine-2-carboxylic acid amide, Ic-5

Treat 1H-pyrrolo[2,3-c]pyridine-2-carboxylic acid amide 6c-1 (1.0 equiv) in DMF (100 mL) with bis-(3-chlorophenyl)disulfide (1.0 equiv) as described above in General Procedure IVb to give Ic-5 as an ivory solid: $^1$H NMR (DMSO-d,) δ 12.8 (bs, 1H), 8.87 (s, 1H), 8.2 (d, J=5.3 Hz, 1H) overlapping with 8.17 (bs, 1H), 7.82 (bs, 1H), 7.41 (d, J=5.4 Hz, 1H), 7.2 (m, 2H), 7.05 (s, 1H), 6.95 (d, J=7.3 Hz, 1H); m/z=304 (M+H).

3-(2-Trifluoromethyl-phenylsulfanyl)-1H-pyrrolo[2,3-c]pyridine-2-carboxylic acid amide, Ic-6

Treat 1H-pyrrolo[2,3-c]pyridine-2-carboxylic acid amide 6c-1 (1.0 equiv) in DMF (100 mL) with bis-(2-trifluoromethyldiphenyl)disulfide (1.0 equiv) as described above in General Procedure IVb to provide Ic-6 as a ivory colored solid: $^1$H NMR (DMSO-d$_6$) δ 12.9 (bs, 1H), 8.9 (bs, 1H), 8.19 (m, 2H), 7.79 (m, 1H), 7.33 (m, 2H), 7.46 (d, J=5.5 Hz, 1H), 7.14 (m, 1H), 6.75 (dd, J=1.3, 7.5 Hz, 1H); m/z=338 (M+H).

3-(2-Trifluoromethoxy-phenylsulfanyl)-1H-pyrrolo[2,3-c]pyridine-2-carboxylic acid amide, Ic-7

Treat 1H-pyrrolo[2,3-c]pyridine-2-carboxylic acid amide 6c-1 (1.0 equiv) in DMF (100 mL) with bis-(2-trifluoromethoxyphenyl)disulfide (1.0 equiv) as described above in General Procedure IVb to give Ic-7 as a tan solid: $^1$H NMR (DMSO-d$_6$) δ 12.8 (bs, 1H), 8.89 (s, 1H), 8.2 (d, J=5.3 Hz, 1H) overlapping with 8.14 (bs, 1H), 7.8 (bs, 1H), 7.36 (m, 2H), 7.1 (dd, J=1.0, 8.3 Hz, 1H), 6.98 (m, 2H); m/z=354 (M+H).

3-(2-Methoxy-phenylsulfanyl)-1H-pyrrolo[2,3-c]pyridine-2-carboxylic acid amide, Ic-8

Treat 1H-pyrrolo[2,3-c]pyridine-2-carboxylic acid amide 6c-1 (1.0 equiv) in DMF (100 mL) with (2-methoxy-diphenyl)disulfide (1.0 equiv) as described above in General Procedure IVb to provide Ic-8 as an ivory colored solid: $^1$H NMR (DMSO-d$_6$) δ 12.40 (bs, 1H), 8.89 (bs, 1H), 8.3-8.16 (m, 1H), 7.86 (s, 1H) overlapping with 7.77 (m, 1H), 7.46 (d, J=5.5 Hz, 1H), 7.14 (m, 1H), 7.03 (dd, J=1.0, 8.3 Hz, 1H), 6.75 (dd, J=1.3, 7.5 Hz, 1H), 6.50 (dd, J=1.5, 7.8 Hz, 1H), 3.89 (s, 3H); m/z=300.1 (M+H).

3-(Pyridin-2-sulfanyl)-1H-pyrrolo[2,3-c]pyridine-2-carboxylic acid amide, Ic-9

Add to 1H-pyrrolo[2,3-c]pyridine-2-carboxylic acid amide (1.0 equiv) in DMF (100 mL), 2,2'-dipyridyl disulfide (Aldrithiol 2, 1.1 equiv) as described in General Procedure IVb to provide Ic-9 as an ivory colored solid: $^1$H NMR (DMSO-d$_6$) δ 12.75 (bs, 1H), 8.86 (s, 1H), 8.35 (dd, 1H, J=14, 4.5 Hz), 8.19 (dd, 1H, J=1, 4 Hz), 8.1 (bs, 1H), 7.85 (bs, 1H), 7.54 (dd, 1H, J=1.8, 7.5 Hz), 7.42 (d, J=5.5 Hz, 1H), 7.10 (dd, 1H, J=4.9, 7.4 Hz), 6.74 (d, 1H, J=8.1 Hz), m/z=271.1 (M+H).

TABLE 1

3-Substituted-1H-pyrrolo[3,2-b]pyridine-2-carboxylic acid amides Ia

| Cmpd No. | R$_1$ | R$_2$ | R$_3$X | R$_4$ |
|---|---|---|---|---|
| Ia-1 | H | NH$_2$ | C$_6$H$_5$S | H |
| Ia-2 | H | NH$_2$ | 3-F—C$_6$H$_4$S | H |
| Ia-3 | H | NH$_2$ | 3-Cl—C$_6$H$_4$S | H |
| Ia-4 | H | NH$_2$ | 3-Br—C$_6$H$_4$S | H |
| Ia-5 | H | NH$_2$ | 2-Cl—C$_6$H$_4$S | H |
| Ia-6 | H | NH$_2$ | 4-Cl—C$_6$H$_4$S | H |
| Ia-7 | H | NH$_2$ | 2,4-(Cl)$_2$—C$_6$H$_3$S | H |
| Ia-8 | H | NH$_2$ | 2-F—C$_6$H$_4$S | H |
| Ia-9 | H | NH$_2$ | 2,3-(Cl)$_2$—C$_6$H$_3$S | H |
| Ia-10 | H | NH$_2$ | 2-CF$_3$—C$_6$H$_4$S | H |
| Ia-11 | H | NH$_2$ | 3-CF$_3$—C$_6$H$_4$S | H |
| Ia-12 | H | NH$_2$ | 2-NH$_2$—C$_6$H$_4$S | H |
| Ia-13 | H | NH$_2$ | 2,5-(Cl)$_2$—C$_6$H$_3$S | H |
| Ia-14 | H | NH$_2$ | 2-CH$_3$O—C$_6$H$_4$S | H |
| Ia-15 | H | NH$_2$ | 3-CH$_3$O—C$_6$H$_4$S | H |
| Ia-16 | H | NH$_2$ | 3-NH$_2$—C$_6$H$_4$S | H |
| Ia-17 | H | NH$_2$ | 4-NO$_2$—C$_6$H$_4$S | H |
| Ia-18 | H | NH$_2$ | 3-NO$_2$—C$_6$H$_4$S | H |
| Ia-19 | H | NH$_2$ | 2-CH$_3$—C$_6$H$_4$S | H |
| Ia-20 | H | NH$_2$ | 4-CH$_3$—C$_6$H$_4$S | H |
| Ia-21 | H | NH$_2$ | 3,5-(CH$_3$)$_2$—C$_6$H$_3$S | H |
| Ia-22 | H | NH$_2$ | 3-CH$_3$—C$_6$H$_4$S | H |
| Ia-23 | H | NH$_2$ | 2-CH$_3$CH$_2$—C$_6$H$_4$S | H |
| Ia-24 | H | NH$_2$ | 3-CF$_3$O—C$_6$H$_4$S | H |
| Ia-25 | H | NH$_2$ |  | H |
| Ia-26 | H | NH$_2$ | 2-pyridinylS | H |
| Ia-27 | H | NH$_2$ | 4-pyridinylS | H |
| Ia-28 | H | NH$_2$ | 2-thienylS | H |
| Ia-29 | CH$_3$ | NH$_2$ | C$_6$H$_5$S | H |
| Ia-30 | H | NHCH$_3$ | 3-CF$_3$O—C$_6$H$_4$S | H |
| Ia-31 | H | NHCH$_3$ | 3-Cl—C$_6$H$_4$S | H |
| Ia-32 | H | NHCH$_3$ | 3-F—C$_6$H$_4$S | H |
| Ia-33 | H | NHCH$_3$ | C$_6$H$_5$S | H |
| Ia-34 | CH$_3$ | NH$_2$ | C$_6$H$_5$S | H |
| Ia-35 | H | NH$_2$ | 3-F—C$_6$H$_4$S | 5-CH$_3$O |
| Ia-36 | H | NH$_2$ | 3-CH$_3$O—C$_6$H$_4$S | 5-CH$_3$O |
| Ia-37 | CH$_3$(CH$_2$)$_2$ | NH$_2$ | C$_6$H$_5$S | H |

TABLE 2

3-Substituted-1H-pyrrolo[3,2-c]pyridine-2-carboxylic acid amides Ib

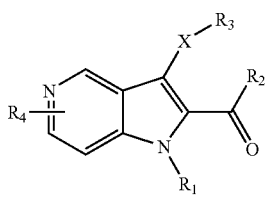

| Cmpd No. | $R_1$ | $R_2$ | $R_3X$ | $R_4$ |
|---|---|---|---|---|
| Ib-1 | H | $NH_2$ | $C_6H_5S$ | H |
| Ib-2 | H | $NH_2$ | 3-F—$C_6H_4S$ | H |
| Ib-3 | H | $NH_2$ | 4-Cl—$C_6H_4S$ | H |

TABLE 3

3-Substituted-1H-pyrrolo[2,3-c]pyridine-2-carboxylic acid amides Ic

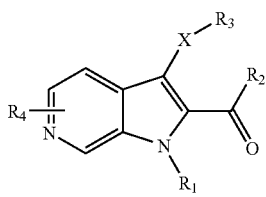

| Cmpd No. | $R_1$ | $R_2$ | $R_3X$ | $R_4$ |
|---|---|---|---|---|
| Ic-1 | H | $NH_2$ | $C_6H_5S$ | H |
| Ic-2 | H | $NH_2$ | $C_6H_5S(O)2$ | H |
| Ic-3 | H | $NH_2$ | 3-F—$C_6H_4S$ | H |
| Ic-4 | H | $NH_2$ | 3-$CH_3O$—$C_6H_4S$ | H |
| Ic-5 | H | $NH_2$ | 3-Cl—$C_6H_4S$ | H |
| Ic-6 | H | $NH_2$ | 2-$CF_3$—$C_6H_4S$ | H |
| Ic-7 | H | $NH_2$ | 2-$CF_3O$—$C_6H_4S$ | H |
| Ic-8 | H | $NH_2$ | 2-$CH_3O$—$C_6H_4S$ | H |
| Ic-9 | H | $NH_2$ | 2-pyridinylS | H |

Biological Examples

Casein Kinase Epsilon $^{33}$P-ATP Filter Plate Assay for Screening CK1ε Inhibitors Purpose: This assay measures the effect of compounds to inhibit the phosphorylation of the substrate casein by the enzyme casein kinase 1ε using an in vitro $^{33}$P-ATP filtration assay. Compounds are tested at five concentrations in duplicate in order to generate $IC_{50}$ values or % inhibition at a 10 micromolar concentration that are summarized in Table 4.

Materials:

Equipment:
Beckman Biomek 2000 Liquid Handling Robot
Beckman Multimek 96 Automated 96 Channel Pipettor
Millipore Vacuum Manifold Basic Kit # MAVM0960R
Titertek Multidrop Liquid Dispenser
Packard TopCount NXT Liquid Scintillation Counter
Plates:
Costar EIA/RIA Plate #9018
Falcon 96 well U bottom Polystyrene Plate #353910
Millipore Multiscreen 96 well Filtration Plates #MAPH-NOB50
Millipore Multiscreen TopCount Adapter Plates #SE3M203V6
Chemicals:
EGTA from SIGMA #E-3889
Casein (dephosphorylated) from SIGMA #C4032
ATP from SIGMA #A-7699
DTT from Fisher Biotech #BP1725
Trichloroacetic Acid from SIGMA #T-6399
γ-$^{33}$P-ATP 1 mCi/37 MBq from Perkin Elmer Life Sciences #NEG-602H
Enzyme:
Casein Kinase 1ε final concentration 0.58 mg/ml obtained from fermentation and purification processes performed by Aventis Pharmaceuticals Inc., France. The above are stored as 100 μL aliquots at minus 80° C.
Compounds:
Compounds for testing are supplied as frozen 10 mM compound stock dissolved in 100% DMSO.

Assay Conditions:

Final total assay volume per well is equal to 50 μL made up as follows:

5 μL of diluted compound stock (10, 1, 0.1, 0.01 or 0.001 μM),
5 μL of dephosphorylated casein final concentration 0.2 μg/μL,
20 μL of CK1ε final concentration 3 ng/μL, and
20 μL of γ-$^{33}$P-ATP final concentration 0.02 μCi/μL mixed with cold ATP (10 μM final).

Methodology:

1. 500 mL of fresh assay buffer is made: 50 mM Tris pH 7.5, 10 M $MgCl_2$, 2 mM DTT and 1 mM EGTA 2. Compounds to be evaluated are obtained as 10 μL of 10 mM stock dissolved in 100% DMSO. Using a Biomek 2000 liquid handling robot, serial dilutions are made to yield 10, 1, 0.1, 0.01 and 0.001 μM final compound dilutions added as 5 μL additions to Falcon U bottom plates. Typically 8 compounds are tested per 96 well plate with column 1 and 12 serving as control wells. A routine screening assay will consist of 32 compounds, which equals 4 assay plates.

3. Assay plate maps are set up according to the following pattern CK1ePlateMap.xls

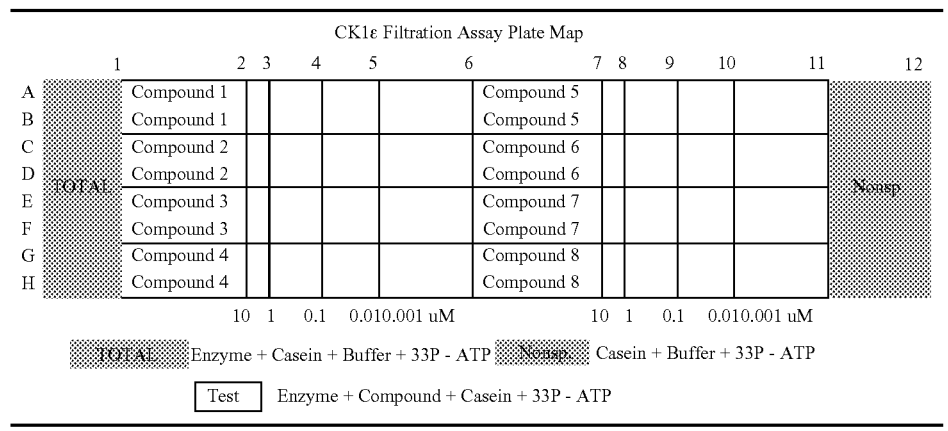

4. Once 5 μL of compound has been added as indicated, 5 μL of dephosphorylated casein (dissolved in distilled H₂O 0.2 μg/μL) and 20 μL CK1ε (3 ng/μL) are added to the appropriate wells.
5. Finally 20 μL γ-$^{33}$P-ATP (0.02 μCi/μL)/10 μM cold ATP are added (equals approximately 2×10⁶ CPM per well).
6. The Falcon U-Bottom assay plate containing the above 50 μL reaction volume is vortexed and then incubated at room temperature for 2 hours.
7. At the end of 2 hours, the reaction is stopped by the addition of 65 μL of ice cold 2 mM cold ATP (made up in assay buffer) to the assay plates using a Beckman Multimek
8. At the same time 25 μL 100% ice cold TCA made up in distilled H₂O is added to a matching number of Millipore MAPH filter plates.
9. Using a handheld 8-channel pipettor, 100 μL of the reaction mixture is transferred from the Falcon U-Bottom Plate to the Millipore MAPH filter plates presoaked with TCA.
10. The Millipore MAPH filter plates are mixed gently and allowed to sit at room temperature for at least 30 minutes to precipitate the proteins.
11. After 30 minutes the filter plates are placed on a Millipore vacuum manifold and filtered at no more than 8 mm Hg as the MAPH filters tend to "air lock" at higher vacuum settings.
12. The filter plates are sequentially washed and filtered with 2×150 μL 20% TCA, 2×150 μL 10% TCA and 2×150 μL 5% TCA (total of 6 washes per plate/900 μL per well).
13. Plates are allowed to dry overnight at room temperature. The next day 40 μL Packard Microscint-20 Scintillation Fluid is added per well using a Titertek Multidrop dispenser; the plates are sealed and counted for 2 minutes/well in a Packard Topcount NXT Scintillation Counter (CPM values/well are captured).

Calculation:
1. Counts Per Minute (CPM) data is captured and imported into a proprietary data calculation and archiving database (Activity Base by IDBS version 5.0).
2. Column 1 for each plate reflects total phosphorylation activity of the enzyme in the absence of any inhibiting compound and thus represents 100%. Column 12 reflects any nonspecific phosphorylation/retained radioactivity activity in the absence of inhibiting compound and enzyme. Typically we see approximately 1% of Total CPMs that are "nonspecific".
3. By having determined the "total" and "nonspecific" CPMs for each plate one is able to determine the % inhibition of the enzyme's ability to phosphorylate the substrate for each concentration of test compound. This % inhibition data is used to calculate an IC$_{50}$ value (concentration at which a compound is able to inhibit the enzyme activity by 50%) for a compound using a non-linear curve fit program contained with the Activitybase calculation protocol (DG0027-CK1-D-BL) (Study: RESR$_{0290}$).
4. Kinetic studies have determined the K$_m$ value for ATP to be 21 μM in this assay system.

Casein Kinase 1δ Streptavidin Affinity Membrane Plate Assay for CKIδ inhibitors Purpose: To evaluate test compounds for CKIδ activity in Streptavidin Affinity Membrane (SAM) Biotin Capture Plate (Promega V7542)

Supplies and reagents

HEPES Sigma # H3375 MW=238.3; β-Glycerol phosphate Sigma # G-9891 MW=216.0;

EDTA 0.5M, pH 8.0 GibcoBRL; Sodium orthovanadate ACROS # 205330500 MW=183.9;

DTT (DL-dithiothreitol) Sigma # D-5545 MW=154.2; Magnesium Chloride ACROS # 41341-5000 MW=203.3; ATP Sigma # A-7699 MW=551.1; γ$^{33}$P ATP NEN # NEG602H;

Casein Kinase 1δ Sigma # C4455; Casein Kinase 1 substrate New England Peptide Biotin-RRKDLHD-DEEDEAMSITA MW=2470

Prepare Kinase Buffer (KB, 100 mL) as follows:

| | |
|---|---|
| 50 mM HEPES, pH 8.0 | 5 mL of 1M stock |
| 10 mM MgCl | 1 mL of 1M stock |
| 10 mM β-glycerophosphate | 1 mL of 1M stock |
| 2.5 mM EDTA | 500 μL of 500 mM stock |
| 1 mM sodium orthovanadate | 100 μL of 1M stock |
| 1 mM DTT | 100 μL of 1M stock |
| water | 92.3 mL |

Prepare ATP Master Mix as follows:

Prepare 1 mL of a 1M ATP solution in water (1M ATP stock).

To 12 mL KB:
  Add 12 µl of 1M ATP solution, then
  Add 12 µl of $^{33}$P ATP (10 µCi/ul), NEG602H, Perkin Elmer Prepare the reaction plate and conduct the assay as follows:
1. Add 10 µL of KB per well with or without the test compound inhibitor to reaction plate wells
2. Add 60 µL of KB per well
3. Add 10 µL of 500 µM Peptide Substrate per well
4. Bring plate up to 37° C.
5. Add 10 µL of 1:10 dilution of CK1δ per well=0.42 µg or 0.68 units
6. Initiate the reaction with 10 µL of ATP Master Mix per well
7. Place the reaction plate in 37° C. incubator for 10 min.
8. Stop the reaction with 10 µL of 1M ATP. Transfer 20 µL to the SAM Plate and let stand 10 min at room temperature.
9. Wash three times with 100 µL of 2M NaCl solution, then three times with 100 µL of 2M NaCl and 1% $H_3PO_4$ solutions and then three times with 100 µl of water on a vacuum manifold.
10. Dry the filter plate under a lamp for 30 min.
11. Seal bottom of plate and add 20 µL of MicroScint 20
12. Read in TOPCOUNT Cellular Circadian Assay Experimental Procedures Cell culture: Mper1-luc Rat-1 fibroblasts (P2C4) cultures were split every 3-4 days (~10-20% confluence) onto 150 cm$^2$ vented polystyrene tissue culture flasks (Falcon # 35-5001) and maintained in growth media [EMEM (Cellgro #10-010-CV); 10% fetal bovine serum (FBS; Gibco #16000-044); and 50 I.U./mL penicillin-streptomycin (Cellgro #30-001-Cl)] at 37° C. and 5% $CO_2$.

Stable transfection: Rat-1 fibroblast cultures at 30-50% confluence were co-transfected with vectors containing the Zeocin resistance selectable marker for stable transfection and an mPer-1 promoter-driven luciferase reporter gene. After 24-48 hours, cultures were split onto 96 well plates and maintained in growth media supplemented with 50-100 µg/mL Zeocin (Invitrogen #45-0430) for 10-14 days. Zeocin-resistant stable transfectants were assessed for reporter expression by supplementing growth media with 100 µM luciferin (Promega #E1603) and assaying luciferase activity on a TopCount scintillation counter (Packard Model #C384V00). Rat-1 clones expressing both Zeocin-resistance and mPer1-driven luciferase activity were synchronized by 50% horse serum [HS (Gibco #16050-122)] serum shock and assessed for circadian reporter activity. Mper1-luc Rat-1 fibroblasts clone P2C4 was selected for compound testing.

Synchronization protocol: Mper1-luc Rat-1 fibroblasts (P2C4) were plated (40-50% confluence) onto opaque 96-well tissue culture plates (PerkinElmer #6005680) and maintained in growth media supplemented with 100 µg/mL Zeocin (Invitrogen #45-0430) until cultures reached 100% confluence (48-72 h). Cultures were synchronized with 100 µL synchronization media [EMEM (Cellgro #10-010-CV); 100 I.U./mL penicillin-streptomycin (Cellgro #30-001-Cl); 50% HS (Gibco #16050-122)] for 2 hours at 37° C. and 5% CO2. After synchronization, cultures were rinsed with 100 µL EMEM (Cellgro #10-010-CV) for 10 minutes at room temperature. After rinse, media was replaced with 300 µL CO2-independent media [CO2I (Gibco #18045-088); 2 mM L-glutamine (Cellgro #25-005-C1); 100 I.U./mL penicillin-streptomycin (Cellgro #30-001-C1); 100 µM luciferin (Promega #E 1603)]. Compounds tested for circadian effects were added to $CO_2$-independent media in 0.3% DMSO (final concentration). Cultures were immediately sealed with TopSeal-A film (Packard #6005185) and transferred for luciferase activity measurement.

Automated Circadian Reporter Measurement: After synchronization, assay plates were maintained at 37° C. in a tissue culture incubator (Forma Scientific Model #3914). In Vivo luciferase activity was estimated by measuring relative light output on a TopCount scintillation counter (Packard Model #C384V00). Plates were transferred from incubator to reader using an ORCA robotic arm (Beckman Instruments) and SAMI-NT automated scheduling software (Version 3.3; SAGIAN/Beckman Instruments).

Data Analysis: Microsoft Excel and XLfit (Version 2.0.9; IDBS) were used to import, manipulate and graph data. Period analysis was performed either by determining the interval between relative light output minima over several days or by Fourier Transform. Both methods produced nearly identical period estimation over a range of circadian periods. Potency is reported as $EC_{\Delta t+1h}$, which is presented as the effective micromolar concentration that induced a 1 hour lengthening of period. The data was analyzed by fitting a hyperbolic curve to the data expressed as period change (y-axis) versus the concentration of test compound (x-axis) in XLfit and the $EC_{\Delta t+1h}$ was interpolated from this curve.

TABLE 4

Biological Data

| Cmpd No. | Casein Kinase Iε $^{33}$P-ATP Filter Plate Assay IC$_{50}$ (nM) | Cell Assay EC$_{\Delta t+1 h}$ (µM) |
|---|---|---|
| Ia-1 | 36* | 0.27 |
| Ia-2 | 74* | 0.51 |
| Ia-3 | 26* | 0.31 |
| Ia-4 | 25* | 0.12 |
| Ia-5 | 6531* | 1.13 |
| Ia-6 | 491* | 13.8 |
| Ia-7 | >10$^4$ | |
| Ia-8 | 531 | 0.75 |
| Ia-9 | >10$^4$ | |
| Ia-10 | 2889 | 2.94 |
| Ia-11 | 709 | |
| Ia-12 | 36* | 0.44 |
| Ia-13 | >10$^4$ | |
| Ia-14 | 669 | |
| Ia-15 | 109* | 1.1 |
| Ia-16 | 424* | |
| Ia-17 | 9788 | |
| Ia-18 | 186* | >10 |
| Ia-19 | 140 | |
| Ia-20 | 261 | >10 |
| Ia-21 | 6876 | |
| Ia-22 | 73* | >10 |
| Ia-23 | 6482 | |
| Ia-24 | 219 | |
| Ia-25 | 1553 | 2.26 |
| Ia-26 | 190 | |
| Ia-27 | 2978 | |
| Ia-28 | 53* | |
| Ia-29 | >10$^4$ | |
| Ia-30 | >10$^4$ | |
| Ia-31 | >10$^4$ | |
| Ia-32 | >10$^4$ | |
| Ia-33 | >10$^4$ | |
| Ia-34 | 339* | |
| Ia-35 | 896* | |

TABLE 4-continued

Biological Data

| Cmpd No. | Casein Kinase Iε $^{33}$P-ATP Filter Plate Assay IC$_{50}$ (nM) | Cell Assay EC$_{\Delta\tau+1\,h}$ (μM) |
|---|---|---|
| Ia-36 | 86 | |
| Ia-37 | 123 | |
| Ib-1 | 1127* | |
| Ib-2 | 466 | |
| Ib-3 | 7957 | |
| Ic-1 | 388* | |
| Ic-2 | >10$^4$* | |
| Ic-3 | 1844 | |
| Ic-4 | 397 | |
| Ic-5 | 375 | |
| Ic-6 | 759 | |
| Ic-7 | 1286 | |
| Ic-8 | 442 | |
| Ic-9 | 291 | |

*denotes average of 2 or more determinations.

What is claimed is:

1. A compound of formula (I)

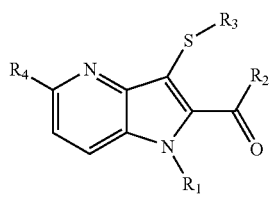

(I)

wherein:
R$_1$ is H or C$_{1-6}$alkyl;
R$_2$ is NR$_5$R$_6$;
R$_3$ is aryl or heterocycle;
R$_4$ is H, C$_{1-6}$alkyl, C$_{1-6}$alkoxy, CF$_3$, halogen, S—C$_{1-6}$alkyl, —SH, —NH$_2$ or NR$_5$R$_6$;
R$_5$ is H or C$_{1-6}$alkyl;
R$_6$ is H or C$_{1-6}$alkyl.

2. The compound according to claim 1 wherein R$_1$ is H or C$_{1-6}$alkyl, R$_5$ is H, R$_6$ is H or C$_{1-6}$alkyl, and R$_3$ is aryl.

3. The compound according to claim 2 selected from the group consisting of: 1-methyl-3-phenylsulfanyl-1H-pyrrolo[3,2-b]pyridine-2-carboxylic acid methylamide, 1-methyl-3-phenylsulfanyl-1H-pyrrolo[3,2-b]pyridine-2-carboxylic acid amide, and 3-phenylsulfanyl-1-propyl-1H-pyrrolo[3,2-b]pyridine-2-carboxylic acid amide.

4. The compound according to claim 1 wherein R$_1$, R$_4$ and R$_5$ are each H, R$_3$ is aryl and R$_6$ is C$_{1-6}$alkyl.

5. The compound according to claim 4 selected from the group consisting of:
3-(3-trifluoromethyoxyphenylsulfanyl-1H-pyrrolo[3,2-b]pyridine-2-carboxylic acid methylamide,
3-(3-chlorophenylsulfanyl-1H-pyrrolo[3,2-b]pyridine-2-carboxylic acid methylamide,
3-(3-fluorophenylsulfanyl-1H-pyrrolo[3,2-b]pyridine-2-carboxylic acid methylamide, and
3-phenylsulfanyl-1H-pyrrolo[3,2-b]pyridine-2-carboxylic acid methylamide.

6. The compound according to claim 1 wherein R$_1$, R$_4$, R$_5$ and R$_6$ is each H and R$_3$ is heterocycle.

7. The compound according to claim 6 is selected from the group consisting of:

3-(quinolin-8-ylsulfanyl)-1H-pyrrolo[3,2-b]pyridine-2-carboxylic acid amide,
3-(pyridin-2-sulfanyl)-1H-pyrrolo[3,2-b]pyridine-2-carboxylic acid amide,
3-(pyridin-4-sulfanyl)-1H-pyrrolo[3,2-b]pyridine-2-carboxylic acid amide, and
3-(thiophen-2-ylsulfanyl)-1H-pyrrolo[3,2-b]pyridine-2-carboxylic acid amide.

8. The compound according to claim 6 wherein R$_1$, R$_5$ and R$_6$ are each H and R$_3$ is aryl.

9. The compound according to claim 1 selected from the group consisting of:
3-phenylsulfanyl-1H-pyrrolo[3,2-b]pyridine-2-carboxylic acid amide,
3-(3-fluorophenylsulfanyl)-1H-pyrrolo[3,2-b]pyridine-2-carboxylic acid amide,
3-(3-chlorophenylsulfanyl)-1H-pyrrolo[3,2-b]pyridine-2-carboxylic acid amide,
3-(3-bromophenylsulfanyl)-1H-pyrrolo[3,2-b]pyridine-2-carboxylic acid amide,
3-(2-chlorophenylsulfanyl)-1H-pyrrolo[3,2-b]pyridine-2-carboxylic acid amide,
3-(4-chlorophenylsulfanyl)-1H-pyrrolo[3,2-b]pyridine-2-carboxylic acid amide,
3-(2,4-dichlorophenylsulfanyl)-1H-pyrrolo[3,2-b]pyridine-2-carboxylic acid amide,
3-(2-fluorophenylsulfanyl)-1H-pyrrolo[3,2-b]pyridine-2-carboxylic acid amide,
3-(2,3-dichlorophenylsulfanyl)-1H-pyrrolo[3,2-b]pyridine-2-carboxylic acid amide,
3-(2-trifluormethylphenylsulfanyl)-1H-pyrrolo[3,2-b]pyridine-2-carboxylic acid amide, 3-(3-trifluoromethylphenylsulfanyl)-1H-pyrrolo[3,2-b]pyridine-2-carboxylic acid amide,
3-(2-aminophenylsulfanyl)-1H-pyrrolo[3,2-b]pyridine-2-carboxylic acid amide,
3-(2,5-dichloro-phenylsulfanyl)-1H-pyrrolo[3,2-b]pyridine-2-carboxylic acid amide,
3-(2-methoxy-phenylsulfanyl)-1H-pyrrolo[3,2-b]pyridine-2-carboxylic acid amide,
3-(3-methoxy-phenylsulfanyl)-1H-pyrrolo[3,2-b]pyridine-2-carboxylic acid amide,
3-(3-amino-phenylsulfanyl)-1H-pyrrolo[3,2-b]pyridine-2-carboxylic acid amide,
3-(4-nitro-phenylsulfanyl)-1H-pyrrolo[3,2-b]pyridine-2-carboxylic acid amide,
3-(3-nitro-phenylsulfanyl)-1H-pyrrolo[3,2-b]pyridine-2-carboxylic acid amide,
3-o-tolylsulfanyl-1H-pyrrolo[3,2-b]pyridine-2-carboxylic acid amide,
3-p-tolylsulfanyl-1H-pyrrolo[3,2-b]pyridine-2-carboxylic acid amide,
3-(3,5-dimethyl-phenylsulfanyl)-1H-pyrrolo[3,2-b]pyridine-2-carboxylic acid amide,
3-m-tolylsulfanyl-1H-pyrrolo[3,2-b]pyridine-2-carboxylic acid amide,
3-(2-ethyl-phenylsulfanyl)-1H-pyrrolo[3,2-b]pyridine-2-carboxylic acid amide,
3-(3-trifluoromethoxy-phenylsulfanyl)-1H-pyrrolo[3,2-b]pyridine-2-carboxylic acid, amide,
3-(3-fluoro-phenylsulfanyl)-5-methoxy-1H-pyrrolo[3,2-b]pyridine-2-carboxylic acid amide, and
3-(3-methoxy-phenylsulfanyl)-5-methoxy-1H-pyrrolo[3,2-b]pyridine-2-carboxylic acid amide.

10. A pharmaceutical composition comprising one or more pharmaceutical carriers and a therapeutically effective amount of a compound, or a pharmaceutically acceptable salt thereof, of formula (I):

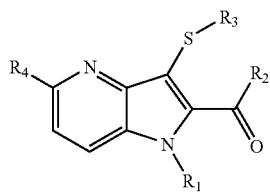

(I)

wherein:
$R_1$ is H or $C_{1-6}$alkyl;
$R_2$ is $NR_5R_6$;
$R_3$ is aryl or heterocycle;
$R_4$ is H, $C_{1-6}$alkyl, $C_{2-6}$alkenyl, $C_{2-6}$alkynyl, $C_{1-6}$alkoxy, $CF_3$, halogen, SH, S—$C_{1-6}$alkyl, $NO_2$, $NH_2$ or $NR_5R_6$;
$R_5$ is H or $C_{1-6}$alkyl;
$R_6$ is H or $C_{1-6}$alkyl.

11. The pharmaceutical composition of claim 10 wherein said pharmaceutical carrier is selected from the group consisting of diluents, binders, solvents, disintegrating agents, lubricants, sweetening agents, bulking agents, permeation enhancers, and solvents.

* * * * *